United States Patent
Schwabe et al.

(10) Patent No.: US 7,730,078 B2
(45) Date of Patent: Jun. 1, 2010

(54) ROLE BASED INTERNET ACCESS AND INDIVIDUALIZED ROLE BASED SYSTEMS TO VIEW BIOMETRIC INFORMATION

(75) Inventors: Jackie A. Schwabe, Milwaukee, WI (US); Gregory A. Wischstadt, Wales, WI (US); Brett A. Quas, Pewaukee, WI (US)

(73) Assignee: Honeywell HomMed LLC, Brookfield, WI (US)

( * ) Notice: Subject to any disclaimer, the term of this patent is extended or adjusted under 35 U.S.C. 154(b) by 183 days.

(21) Appl. No.: 11/536,239

(22) Filed: Sep. 28, 2006

(65) Prior Publication Data
US 2008/0082536 A1    Apr. 3, 2008

(51) Int. Cl.
*G06F 12/00*    (2006.01)
*G06F 17/30*    (2006.01)

(52) U.S. Cl. .................. 707/758; 707/769; 707/781; 707/783; 707/784

(58) Field of Classification Search ............ None
See application file for complete search history.

(56) References Cited

U.S. PATENT DOCUMENTS

| | | | |
|---|---|---|---|
| 6,402,691 B1 | 6/2002 | Peddicord et al. | |
| 6,505,193 B1 * | 1/2003 | Musgrave et al. | 707/3 |
| 7,469,382 B1 * | 12/2008 | Dwight | 715/738 |
| 2002/0083075 A1 * | 6/2002 | Brummel et al. | 707/102 |
| 2002/0156929 A1 * | 10/2002 | Hekmatpour | 709/310 |
| 2002/0169777 A1 * | 11/2002 | Balajel et al. | 707/10 |
| 2003/0036683 A1 * | 2/2003 | Kehr et al. | 600/300 |
| 2004/0143469 A1 * | 7/2004 | Lutz et al. | 705/7 |
| 2004/0167989 A1 * | 8/2004 | Kline et al. | 709/245 |
| 2004/0243567 A1 * | 12/2004 | Levy | 707/3 |
| 2005/0044409 A1 * | 2/2005 | Betz et al. | 713/201 |
| 2005/0060198 A1 * | 3/2005 | Bayne | 705/2 |
| 2006/0052945 A1 * | 3/2006 | Rabinowitz et al. | 702/20 |
| 2006/0136486 A1 * | 6/2006 | Correa | 707/102 |
| 2006/0206429 A1 * | 9/2006 | Martinez | 705/50 |
| 2006/0212452 A1 * | 9/2006 | Cornacchia | 707/10 |
| 2006/0263757 A1 * | 11/2006 | Bender | 434/350 |
| 2007/0004970 A1 * | 1/2007 | Tice | 600/300 |
| 2007/0240231 A1 * | 10/2007 | Haswarey et al. | 726/28 |
| 2007/0270998 A1 * | 11/2007 | Luciano et al. | 700/216 |
| 2008/0033959 A1 * | 2/2008 | Jones | 707/9 |

* cited by examiner

*Primary Examiner*—Jay A Morrison
(74) *Attorney, Agent, or Firm*—Husch Blackwell Sanders Welsh & Kratz

(57) ABSTRACT

A web based application makes data conveniently and readily available to individuals dispersed from a common collection site or database. Individuals can access various levels of retrospective or previously stored data in the database only in accordance with pre-defined roles, or levels which can be established at log on.

20 Claims, 41 Drawing Sheets

TABULAR TRENDS - MICROSOFT INTERNET EXPLORER

FILE  EDIT  VIEW  FAVORITES  TOOLS  HELP

BACK ▽ ⊙ ▽ ⊠ ⊡ ⌂ | 🔍 SEARCH ★ FAVORITES ⊘ | ⊘ ▽ 🖨 ▽ 📁 ▽ W ▽ 🗋 ▽ 🗐 ⌕

ADDRESS: HTTP://W06NT019/CSDEV/LEVEL/TABULAR TRENDS.ASPX  [→ GO]  LINKS »

HONEYWELL
HOMMED                                                        CENTRAL STATION WEB SITE

HOME > PATIENT/FAMILY MEMBER > TABULAR TRENDS                                    LOGOUT

▽ HOME
  ▽ PATIENT/FAMILY MEMBER                    BANKS, CARL
    ▷ TABULAR TRENDS               SELECT PATIENT [BANKS, CARL ▽]
    ▷ PATIENT DEMOGRAPHICS                                           ↙ 104
  ▽ REPORTS

| DATE/TIME | WEIGHT | BLOOD PRESSURE | SPO2 | HR | TEMP | ANSWERS | ADDITIONAL DEVICES |
|---|---|---|---|---|---|---|---|
| 09/20/2006 15:43 (WED) (CDT) | 11.0 | 138/85 | - | 68 | - | 2 NA | - |
| 09/20/2006 08:00 (WED) (CDT) | - | - | - | - | - | - | - |
| 09/19/2006 08:00 (TUE) (CDT) | - | - | - | - | - | - | - |
| 09/18/2006 14:55 (MON) (CDT) | 13.0 | 134/84 | - | 64 | - | 2 NO | - |
| 09/18/2006 08:00 (MON) (CDT) | - | - | - | - | - | - | - |
| 09/17/2006 08:00 (SUN) (CDT) | - | - | - | - | - | - | - |

▷ TABULAR TRENDS
    ▷ GRAPHICAL TRENDS
    ▷ PATIENT INFORMATION
  ▽ MAINTENANCE
    ▷ CHANGE PASSWORD

↙ 7E

LOCAL INTRANET

HONEYWELL
HOMMED

CENTRAL STATION WEB SITE REPORTS          LOGOUT

HOME > REPORTS > PATIENT INFORMATION

INCLUDE: ☑ CONTACTS ☑ INSURERS ☑ PHYSICIANS
BANKS, CARL  ▾  RUN REPORT

PAGE 1 ▾ OF 1   PDF ▾

PATIENT INFORMATION REPORT FOR  BANKS, CARL                                                    MONDAY, SEPTEMBER 25, 2006
PATIENT

| PATIENT NAME | DOB | SSN | MEDICAL ID | EXPORT ID |
|---|---|---|---|---|
| BANKS, CARL | 01/20/1967 | 495-09-0980 | 120-0974 | 123233 |

| ADDRESS | PHONE NUMBER | | GENDER | RACE | HEIGHT |
|---|---|---|---|---|---|
| 120 MAIN ST BROOKFIELD, AR 53045 | 262-789-1987 | | MALE | ASIAN | 720 |

CONTACTS

| CONTACT NAME | RELATIONSHIP | PHONE NUMBER | ROLE TYPE |
|---|---|---|---|
| JAY HAWK | FRIEND | 414-455-0980 | EMER |
| DEAN JONES | FRIEND | 414-456-0980 | EMER |

INSURERS

| INSURER NAME | CONTACT NAME | PHONE NUMBER | PLAN TYPE | GROUP ID | POLICY ID | EFFECTIVE DATE |
|---|---|---|---|---|---|---|
| WPS | JEAN HOOPER | 414-456-0980 | HMO | 1204-098 | | 9/1/2006 |
| MKW1 | SMITH | 414-456-0098 | | 1200-093 | | 9/2/2006 |
| WPS1 | | | | | | |

PHYSICIANS

| PHYSICIAN NAME | ORGANIZATION | PHONE NUMBER | FAX NUMBER | SPECIALITY | ROLE TYPE |
|---|---|---|---|---|---|
| HENRY ANDERSON | HEART FAILURE CLINIC | 555-888-9999 | | INTERNAL MEDICINE | PRIMARY |

HONEYWELL
HOMMED

CENTRAL STATION WEB SITE

LOGOUT

HOME > CLINICIAN > PATIENT LIST

▽ HOME
　▽ CLINICIAN
　　▷ CURRENT STATUS
　　▷ TABULAR TRENDS
　　▷ PATIENT DEMOGRAPHICS
　　▷ PATIENT LIST
　▽ REPORTS
　　▷ TABULAR TRENDS
　　▷ GRAPHICAL TRENDS
　　▷ MULTI PATIENT TRENDS
　　▷ PATIENT COMPLIANCE
　　▷ PATIENT INFORMATION
　▽ MAINTENANCE
　　▷ CHANGE PASSWORD

BANKS, CARL

| PATIENT NAME | MEDICAL ID | PHYSICIAN NAME | INSURER NAME | SERIAL NUMBER | SITE NAME |
|---|---|---|---|---|---|
| ADAMICK, FRANCES | MEDICARE | POWER, JOHN ANTHONY | SUE | 905330701 | HONEYWELL HOMMED QA LAB |
| ARNOLD, WAYNE | MEDICARE | SULLIVAN, LAWRENCE | PATTY | 905330529 | HONEYWELL HOMMED QA LAB |
| BACHER, JOHN | MEDICARE | CULIG, MICHAEL | JAY | 905330718 | HONEYWELL HOMMED QA LAB |
| BANKS, CARL | 120-0974 | ANDERSON, HENRY | MKW1 | 905330528 | HONEYWELL HOMMED AGENCY |
| BETZ, ERWIN | ADVANTRA | CARRELL, ROBERT | SUE R. | | HONEYWELL HOMMED QA LAB |
| BONADIO, DOMINIC | SEC BLUE | JURIGA, BARBARA | | | HONEYWELL HOMMED QA LAB |
| CALHOUN, KELLY | | ANDERSON, HENRY | WPS | | HOMECARE AGENCY |
| DOE, JOHN | | HAGGERTY, EARL | | 905220374 | HOMMED |
| LENDIN, JOHN | MRN 13834 | ATIKINS, BRICE | MEDICARE | | HONEYWELL HOMMED AGENCY |
| NAGEL, NICK | MRN 12124 | WAGNER, BRICE | MEDICARE | | HOMECARE AGENCY |

TABULAR TRENDS REPORT - MICROSOFT INTERNET EXPLORER

FILE EDIT VIEW FAVORITES TOOLS HELP

ADDRESS: HTTP://W06NT019/CSDEV/REPORTS/TABULARTRENDS.ASPX

HONEYWELL
HOMMED

CENTRAL STATION WEB SITE REPORTS

LOGOUT

HOME > REPORTS > TABULAR TRENDS

INCLUDE: ☑ VITALS ☑ GLUCOSE ☑ RESPONSES TO VITALS
☑ ALERTS ☑ ALERT LIMITS HISTORY

REPORT PERIOD: 7 DAYS ▼ | BANKS, CARL ▼ | RUN REPORT

TABULAR TRENDS FOR BANKS, CARL
PATIENT
MONDAY, SEPTEMBER 25, 2006

| PATIENT NAME | DOB | SSN | MEDICAL ID | EXPORT ID |
|---|---|---|---|---|
| BANKS, CARL | 01/20/1967 | 495-09-0980 | 120-0974 | 123233 |
| ADDRESS | PHONE NUMBER | GENDER | RACE | HEIGHT |
| 120 MAIN ST BROOKFIELD, AR 53045 | 262-789-1987 | MALE | ASIAN | 72.0 |
| PHYSICIAN NAME | PHONE NUMBER | FAX NUMBER | ORGANIZATION | |
| HENRY ANDERSON | 555-888-9999 | | HEART FAILURE CLINIC | |

VITALS

| ACK | DATE/TIME | CONDITION | WEIGHT | BP | SPO2 | HR | TEMP | ANSWERS |
|---|---|---|---|---|---|---|---|---|
| NO | 09/20/2006 15:43 (WED)(CDT) | INCOMPLETE | 11.0 | 138/85 | 0 | 68 | 0.0 | 2 NA |
|  | NO QUESTIONS ANSWERED | | | | | | | |
| YES | 09/20/2006 08:00 (WED)(CDT) | NULL | 0.0 | - | 0 | 0 | 0.0 | |
|  | (CENTRAL STATION SEP 20, 2006 8:12 PM) | | | | | | | |
| YES | 09/19/2006 08:00 (TUE)(CDT) | NULL | 0.0 | - | 0 | 0 | 0.0 | |
|  | AN EMPTY PACKET WAS RECEIVED | | | | | | | |
|  | (CENTRAL STATION SEP 20, 2006 12:53 PM) | | | | | | | |
| YES | 09/18/2006 14:55 (MON)(CDT) | COMPLAINT | 13.0 | 134/84 | 0 | 64 | 0.0 | 2 NO |
|  | AUTO ACKNOWLEDGED (HADMIN SEP 18, 2006 7:23 PM) | | | | | | | |
| YES | 09/18/2006 08:00 (MON)(CDT) | NULL | 0.0 | - | 0 | 0 | 0.0 | |
|  | AUTO ACKNOWLEDGED (CENTRAL STATION SEP 18, 2006 7:20 PM) | | | | | | | |

| ID | QUESTIONS |
|---|---|
| 1 | ARE YOU EXPERIENCING MORE DIFFICULTY BREATHING TODAY, COMPARED TO A NORMAL DAY? |
| 2 | ARE YOU MORE TIRED TODAY COMPARED TO A NORMAL DAY? |

MULTI TRENDS REPORT - MICROSOFT INTERNET EXPLORER

FILE  EDIT  VIEW  FAVORITES  TOOLS  HELP

BACK  SEARCH  FAVORITES

ADDRESS: HTTP://W06NT019/CSDEV/REPORTS/MULTITRENDS.ASPX

HONEYWELL
HOMMED

CENTRAL STATION WEB SITE REPORTS

LOGOUT

HOME > REPORTS > MULTI PATIENT TRENDS

INCLUDE: ☑VITALS  ☑GLUCOSE  ☑RESPONSES TO VITALS
         ☑ALERTS  ☑ALERT LIMITS HISTORY

ADAMICK, FRAN ▲
ARNOLD, WAYNE ▼

REPORT PERIOD: 7 DAYS  ▷  RUN REPORT

PAGE 1 OF 1  PDF ▷

MULTI-PATIENT TRENDS REPORT
REPORT OTIONS

REPORT SELECTION
TABULAR TRENDS
REPORT PERIOD
9/18/2006 TO 9/25/2006
PATIENT NAMES
BANKS, CARL
TABULAR TRENDS FOR
PATIENT

MONDAY, SEPTEMBER 25, 2006

| PATIENT NAME | DOB | SSN | MEDICAL ID | EXPORT ID |
|---|---|---|---|---|
| BANKS, CARL | 01/20/1967 | 495-09-0980 | 120-0974 | 123233 |
| ADDRESS | PHONE NUMBER | GENDER | RACE | HEIGHT |
| 120 MAIN ST BROOKFIELD, AR 53045 | 262-789-1987 | MALE | ASIAN | 72.0 |
| PHYSICIAN NAME | PHONE NUMBER | | | ORGANISATION |
| HENRY ANDERSON | 555-888-9999 | FAX NUMBER | | HEART FAILURE CLINIC |

VITALS

MONDAY, SEPTEMBER 25, 2006

| ACK | DATE/TIME | CONDITION | WEIGHT | BP | SPO2 | HR | TEMP | ANSWERS |
|---|---|---|---|---|---|---|---|---|
| NO | 09/20/2006 15:43 (WED)(CDT) | INCOMPLETE | 11.0 | 138/85 | 0 | 68 | 0.0 | 2 NA |
| | 09/20/2006 08:00 (WED)(CDT) | NO QUESTIONS ANSWERED NULL | 0.0 | - | 0 | 0 | 0.0 | |
| YES | (CENTRAL STATION SEP 20, 2006 8:12 PM) | | | | | | | |
| YES | 09/19/2006 08:00 (TUE)(CDT) | AN EMPTY PACKET WAS RECEIVED NULL | 0.0 | - | 0 | 0 | 0.0 | |
| | (CENTRAL STATION SEP 20, 2006 12:53 PM) | | | | | | | |
| YES | 09/18/2006 14:55 (MON)(CDT) | COMPLAINT | 13.0 | 134/84 | 0 | 64 | 0.0 | 2 NO |

DONE  LOCAL INTRANET

*FIG. 8E-3*

HONEYWELL HOMMED  CENTRAL STATION WEB SITE REPORTS  LOGOUT

HOME > REPORTS > PATIENT COMPLIANCE

PDF  DATE RANGE: SEPTE 2005 TO SEPTE 2006
GROUP BY: INSURER  RUN REPORT

PATIENT COMPLIANCE REPORT FROM 9/1/2006 THROUGH 9/30/2006   MONDAY, SEPTEMBER 25, 2006
NO INSURER FOR PATIENT

| PATIENT NAME | DAYS MONITORED | EXPECTED READINGS | RECEIVED READINGS | RED ALERT READINGS | COMPLIANCE |
|---|---|---|---|---|---|
| DOE, JOHN | 34 | 34 | 0 | 0 | 0.0% |
| BONADIO, DOMINIC | 14 | 14 | 0 | 0 | 0.0% |
| TOTALS FOR THE GROUP | 48 | 48 | 0 | 0 | 0.0% |

JAY

| PATIENT NAME | DAYS MONITORED | EXPECTED READINGS | RECEIVED READINGS | RED ALERT READINGS | COMPLIANCE |
|---|---|---|---|---|---|
| BACHER, JOHN | 139 | 139 | 0 | 0 | 0.0% |
| TOTALS FOR THE GROUP | 139 | 139 | 0 | 0 | 0.0% |

MEDICARE

| PATIENT NAME | DAYS MONITORED | EXPECTED READINGS | RECEIVED READINGS | RED ALERT READINGS | COMPLIANCE |
|---|---|---|---|---|---|
| LANDIN, JOAN | 390 | 390 | 17 | 0 | 4.4% |
| TOTALS FOR THE GROUP | 390 | 390 | 17 | 0 | 4.4% |

MEDICARE

| PATIENT NAME | DAYS MONITORED | EXPECTED READINGS | RECEIVED READINGS | RED ALERT READINGS | COMPLIANCE |
|---|---|---|---|---|---|
| NAGEL, NICK | 390 | 390 | 19 | 3 | 4.9% |
| TOTALS FOR THE GROUP | 390 | 390 | 19 | 3 | 4.9% |

MKW1

| PATIENT NAME | DAYS MONITORED | EXPECTED READINGS | RECEIVED READINGS | RED ALERT READINGS | COMPLIANCE |
|---|---|---|---|---|---|
| BANKS, CARL | 34 | 34 | 91 | 33 | 267.6% |
| TOTALS FOR THE GROUP | 34 | 34 | 91 | 33 | 267.6% |

PATTY

| PATIENT NAME | DAYS MONITORED | EXPECTED READINGS | RECEIVED READINGS | RED ALERT READINGS | COMPLIANCE |
|---|---|---|---|---|---|
| ARNOLD, WAYNE | 140 | 140 | 0 | 0 | 0.0% |

FIG. 8E-4

PATIENT INFORMATION REPORT - MICROSOFT INTERNET EXPLORER

FILE  EDIT  VIEW  FAVORITES  TOOLS  HELP

ADDRESS HTTP://W06NT019/CSDEV/REPORTS/PATIENTINFO.ASPX

HONEYWELL
HOMMED

CENTRAL STATION WEB SITE REPORTS    LOGOUT

HOME > REPORTS > PATIENT INFORMATION

INCLUDE: ☑ CONTACTS ☑ INSURERS ☑ PHYSICIANS ☑ ALERT LIMITS

PAGE 1 OF 1   PDF   BANKS, CARL   RUN REPORT

PATIENT INFORMATION REPORT FOR   BANKS, CARL   MONDAY, SEPTEMBER 25, 2006
PATIENT

PATIENT NAME         DOB              SSN            MEDICAL ID      EXPORT ID
BANKS, CARL          01/20/1967       495-09-0980    120-0974        123233

ADDRESS              PHONE NUMBER     GENDER         RACE            HEIGHT
120 MAIN ST BROOKFIELD,  262-789-1987  MALE          ASIAN           72.0
AR 53045
CONTACTS

CONTACT NAME         RELATIONSHIP     PHONE NUMBER                   ROLE TYPE
JAY HAWK             FRIEND           414-455-0980                   ERNER
DEAN JONES           FRIEND           414-456-0980                   ERNER
INSURERS

INSURER NAME         CONTACT NAME     PHONE NUMBER   PLAN TYPE       GROUP ID        POLICY ID       EFFECTIVE DATE
WPS                  JEAN HOOPFER     414-456-0980   HMO             1204-098                        9/1/2006
MKW1                 SMITH            414-456-0098                   1200-093                        9/2/2006
WPS1
PHYSICIANS

PHYSICIAN NAME       ORGANISATION     PHONE NUMBER                   FAX NUMBER      SPECIALITY      ROLE TYPE
HENRY ANDERSON       HEART FAILURE CLINIC  555-888-9999                              INTERNAL MEDICINE  PRIMARY
ALERT LIMITS

WEIGHT               SYSTOLIC         DIASTOLIC                      SPO2            HR              TEMP
8.0 TO 18.0 *        70 TO 200 MMHG * 50 TO 110 MMHG                 NOT ENABLED     26 TO 98 BPM *  NOT ENABLED

GLUCOSE
NOT ENABLED
* INDICATES THAT AN ALERT WILL BE GENERATED, IF AN ALERT IS MISSING

DONE                                                                                                LOCAL INTRANET

ORGANIZATION SETUP - MICROSOFT INTERNET EXPLORER

HONEYWELL
HOMMED

CENTRAL STATION WEB SITE

LOGOUT

HOME > HH ADMINISTRATOR > AGENCY LIST

- ▽ HOME
  - ▽ HH ADMINISTRATOR
    - ▷ AGENCY LIST
    - ▷ USER SETUP
    - ▷ CURRENT STATUS
    - ▷ TABULAR TRENDS
    - ▷ PATIENT DEMOGRAPHICS
    - ▷ PATIENT LIST
  - ▽ REPORTS
    - ▷ TABULAR TRENDS
    - ▷ GRAPHICAL TRENDS
    - ▷ MULTI PATIENT TRENDS
    - ▷ PATIENT COMPLIANCE
    - ▷ PATIENT INFORMATION
  - ▽ MAINTENANCE
    - ▷ CHANGE PASSWORD

| ORGANIZATION NAME | CONTACT NAME | PRIMARY PHONE NUMBER | CREATED DATE |
|---|---|---|---|
| HONEYWELL HOMMED AGENCY | JOHNSON, EMILY | 262-252-6087 | 8/15/2006 5:30:18 PM |
| HOMECARE AGENCY | ROMANO, PETER | 414-252-6088 | 8/17/2006 11:35:53 PM |
| MCLEOD AGENCY | SMITH, JOHN | 414-252-6088 | 8/18/2006 3:12:29 PM |
| HOMECARE AGENCY | ROMANO, PETER | 414-252-6088 | 8/22/2006 2:34:12 PM |
| HONEYWELL HOMMED QA LAB | BUCHTA, ROY | 412-436-2200 | 8/24/2006 1:09:22 PM |
| HOMMED | DEFAULT, SYSTEMINF | 555-555-5555 | 9/12/2006 10:25:57 PM |
| JHJ/ DDJ HEALTHCARE | JJ,DD | 2 | 9/19/2006 12:41:14 PM |

AGENCY DETAIL

ORGANIZATION:
CONTACT FIRST:         MI:       LAST:
STREET 1:
STREET 2:
CITY/STATE/ZIP:                    TYPE: ▽
PRIMARY PHONE:
COUNTRY:      ▽
DEFAULT LOCALE: ENGLISH (UNITED STATES) ▽    TIME ZONE: (GMT-06.00) CENTRAL ▽
PIN:

[ADD] [SAVE] [CANCEL]

HONEYWELL HOMMED

HOME > HT ADMINISTRATOR > PATIENT LIST

CENTRAL STATION WEB SITE

LOGOUT

▽ HOME
- ▽ HT ADMINISTRATOR
  - ▷ AGENCY LIST
  - ▷ USER SETUP
  - ▷ CURRENT STATUS
  - ▷ TABULAR TRENDS
  - ▷ PATIENT DEMOGRAPHICS
  - ▷ PATIENT LIST
- ▽ REPORTS
  - ▷ TABULAR TRENDS
  - ▷ GRAPHICAL TRENDS
  - ▷ MULTI PATIENT TRENDS
  - ▷ PATIENT COMPLIANCE
  - ▷ PATIENT INFORMATION
- ▽ MAINTENANCE
  - ▷ CHANGE PASSWORD

| PATIENT NAME | MEDICAL ID | PHYSICIAN NAME | INSURER NAME | SERIAL NUMBER | SITE NAME |
|---|---|---|---|---|---|
| ALESMAN, MIKE | MRN 12734 | ARORA, FAUZI | MEDICAID | | HONEYWELL HOMMED AGENCY |
| ADER, SHERRY | MRN 12735 | CONNOLO, ZACK | MEDICARE | | HONEYWELL HOMMED AGENCY |
| BANKS, CARL | | ANDERSON, HENRY | | 905330520 | HONEYWELL HOMMED AGENCY |
| BOUMA, THERESA | MRN 22734 | DALINGERS, DON | MEDICARE | | HONEYWELL HOMMED AGENCY |
| BROWER, DANIEL | MRN 12736 | ULINS, JACK | BLUE CROSS & BLUE SHIELD | | HONEYWELL HOMMED AGENCY |
| CALHOUN, KELLY | | ANDERSON, HENRY | WPS | | HOMECARE AGENCY |
| CONLEY, ZACH | MRN 12739 | ATKINS, BRICE | MEDICAID | | HONEYWELL HOMMED AGENCY |
| CRANSTON, GRAHM | MRN 12710 | DERUYRER, SUSAN | MEDICAID | | HONEYWELL HOMMED AGENCY |
| GLUAK, TOM | MRN 12711 | GHAUREE, MAJAN | MEDICARE | | HONEYWELL HOMMED AGENCY |
| GRACE, NOAL | MRN 12712 | GHAUREE, MAJAN | MEDICARE | | HONEYWELL HOMMED AGENCY |

HONEYWELL
HOMMED

CENTRAL STATION WEB SITE REPORTS

LOGOUT

HOME > REPORTS > PATIENT COMPLIANCE

PAGE 1 ▽ OF 6 ▷ ▷|  PDF ▽    DATE RANGE: SEPTE ▽ 2006 ▽ TO SEPTE ▽ 2006 ▽
                                GROUP BY: INSURER    ▷ RUN REPORT

PATIENT COMPLIANCE REPORT FROM 9/1/2006 THROUGH 9/30/2006        MONDAY, SEPTEMBER 25, 2006
NO INSURER FOR PATIENT

| PATIENT NAME | DAYS MONITORED | EXPECTED READINGS | RECEIVED READINGS | RED ALERT READINGS | COMPLIANCE |
|---|---|---|---|---|---|
| QUAKERMANS, JENELLE | 25 | 25 | 0 | 0 | 0.0% |
| SCHAFFER, REBECCA | 25 | 25 | 0 | 0 | 0.0% |
| LOPEZ, JUAN | 25 | 25 | 0 | 0 | 0.0% |
| BONADIO, DOMINIC | 14 | 14 | 0 | 0 | 0.0% |
| TOTALS FOR THE GROUP | 89 | 89 | 0 | 0 | 0.0% |

BLUE CROSS & BLUE SHIELD

| PATIENT NAME | DAYS MONITORED | EXPECTED READINGS | RECEIVED READINGS | RED ALERT READINGS | COMPLIANCE |
|---|---|---|---|---|---|
| BROWER, DANIEL | 25 | 25 | 0 | 0 | 0.0% |
| TOTALS FOR THE GROUP | 25 | 25 | 0 | 0 | 0.0% |

CARESIGHTS

| PATIENT NAME | DAYS MONITORED | EXPECTED READINGS | RECEIVED READINGS | RED ALERT READINGS | COMPLIANCE |
|---|---|---|---|---|---|
| HERTZ, LYON | 25 | 25 | 0 | 0 | 0.0% |
| TOTALS FOR THE GROUP | 25 | 25 | 0 | 0 | 0.0% |

HEART PLAN ONE

| PATIENT NAME | DAYS MONITORED | EXPECTED READINGS | RECEIVED READINGS | RED ALERT READINGS | COMPLIANCE |
|---|---|---|---|---|---|
| LANKE, SUSAN | 25 | 25 | 0 | 0 | 0.0% |
| TOTALS FOR THE GROUP | 25 | 25 | 0 | 0 | 0.0% |

JAY

| PATIENT NAME | DAYS MONITORED | EXPECTED READINGS | RECEIVED READINGS | RED ALERT READINGS | COMPLIANCE |
|---|---|---|---|---|---|
| BACHER, JOHN | 25 | 25 | 0 | 0 | 0.0% |
| TOTALS FOR THE GROUP | 25 | 25 | 0 | 0 | 0.0% |

ROLE BASED INTERNET ACCESS AND INDIVIDUALIZED ROLE BASED SYSTEMS TO VIEW BIOMETRIC INFORMATION

FIELD

The invention pertains to web enabled information retrieval systems. More particularly, the invention pertains to such systems which can make various aspects of previously collected data available to users who may access that data in different roles, or at different access levels.

BACKGROUND

It has been recognized that there are substantial advantages to being able to remotely monitor biometric data at dispersed space locations from a centralized location and to accumulate the required data at such location. One such system has been disclosed in and claimed in Peddicord et al., U.S. Pat. No. 6,402,691B1 assigned to the assignee hereof and incorporated herein by reference. In Peddicord et al., remote monitoring units couple patient/resident information via wired or wireless networks to a centralized monitoring location. Such information can be used at the centralized location to evaluate the medical condition of a particular patient/resident. Decisions can be made as to the necessary additional followup such as adjusting the individual's medication, treatments or diet, as well as additional physical followup.

A variety of different entities, which are not necessarily in the vicinity of the monitoring station, would benefit from ready access to all such collected information. For example, physicians, nurses, therapists, home health professionals and the like all of whom may be located at offices displaced from the central monitoring station, or traveling in their vehicles between the residences of various patients, may have substantial needs to view such information.

Additionally, there are outstanding needs to provide various levels of accessibility to the relevant population. For example, the patient/resident as well as relatives might benefit from access to at least portions of the information. Clinicians, such as physicians, dentists, nurses, physical therapists, home health workers, case managers and the like all might benefit from ready access to different levels of such information. Privacy is an ongoing concern and there is also a need to be able to exclude inappropriate individuals from access.

Thus, there continues to be an ongoing need for systems and methods which would enable health care professionals to access their patients' information on demand. Preferably role based access could be provided to respective individuals using the role of the respective individual as a vehicle to determine which information to make available relative to the respective patient/resident.

There is also an ongoing need to provide access to authorized individuals to the patient/resident information from a variety of locations displaced not only from the patient/resident but also from the central monitoring site where the information might have been collected. Preferably such access could be provided via one or more computer networks and through a variety of data processing units such as hand-held units, laptops, desktop computers and the like, all without limitation in a wired or wireless environment depending on the user's circumstances.

BRIEF DESCRIPTION OF THE DRAWINGS

FIG. 7A illustrates an exemplary tabular trends screen for a patient/resident access level;

FIG. 7B illustrates an exemplary patient demographic screen;

FIG. 7B-1, -2, -3 are respectively contacts, insurers and physician information screens selectable from the screen of FIG. 7B;

FIGS. 7C-1, -2, and -3 taken together illustrate various types of reports available from the system of FIG. 1;

FIG. 8A-1 is an exemplary alert limit status screen in accordance with the invention;

FIGS. 8B-1, -2 illustrate alert limit and standing order screens selectable from the screen of FIG. 8B;

FIG. 8C illustrates demographic information for a selected patient/resident in accordance with the present invention;

FIGS. 8C-1, -2 and -3 taken together illustrate respectively contact information, insurance information and physician information for an individual identified on the screen of FIG. 8C;

FIG. 8D is a patient list screen;

FIG. 8E-1, -2, -3, -4, and -5 taken together illustrate various reports which can be generated by the system of FIG. 1;

FIG. 9 is an agency level set-up screen;

FIG. 10-1 is a screen which lists various agencies which utilize systems in accordance with FIG. 1 at a system administrator level;

FIG. 10-2 illustrates an administrator user setup screen;

FIG. 10-3 illustrates a multi-agency patient list screen; and

FIGS. 10-4, -5, -6, -7, and -8 taken together illustrate various reports generatable at the system administrator level by a system as in FIG. 1.

DETAILED DESCRIPTION

Figure 1:
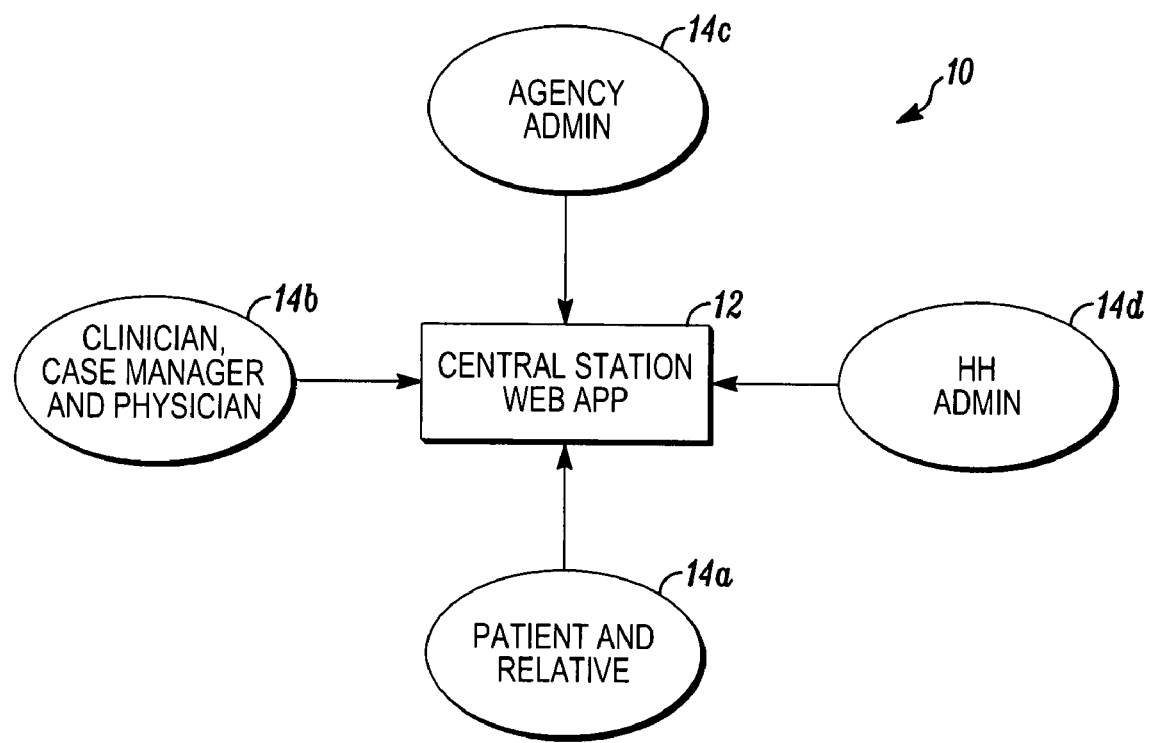
FIG. 1 is an overall functional view of a system which embodies the invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

In accordance with the invention, role based access with respect to an individual's biometric or health care information can be provided via a plurality of computer generated graphical displays associated with the role of the respective individual seeking to view the information. In this regard, different roles, or access levels can be assigned to various types of health care professionals, such as physicians, dentists, psychologists, nurses, therapists, case managers, and the like. Other roles or access levels can be assigned to the patient/resident or relatives thereof.

In another aspect of the invention, each assigned role will have access to specific web pages which display content that is individualized for that role and the respective patient/resident. Roles can be assigned not only to individuals but to institutions such as insurance companies for reimbursement purposes, health care delivery organizations such as home health agencies as well as care monitoring agencies.

In yet another aspect of the invention, different levels of users can be created. A user's level can be specified by log on information, or alternately by a computer readable card or the like or by a user's biometric information. Via a web based application, each of the defined levels or roles can be granted access to patient/resident's information via a role based plurality of displayable web pages.

In yet another aspect of the invention, an authorized individual can access the appropriate patient/resident information associated with the individual's pre-defined role or level through any internet enabled handheld, laptop or desktop computer or processor. Further, the authorized individual can generate reports and enter relevant information, where permitted, in connection with patient/resident condition or treatments.

In yet another aspect of the invention, a plurality of data collection stations or databases can be accessed by different sets of individuals or caregivers in connection with their assigned level or role in the system.

In a disclosed embodiment, the access level or role of an individual seeking entry into the system to review data pertaining to a patient/resident is defined at log on. The defined role or level permits examination or review of only those data sets associated with respective levels.

FIG. 1 is a diagram illustrating aspects of a system 10 in accordance with the present invention. A web based application 12 provides various levels of access to individuals in different roles, for example patient/resident medical data which has been collected in a preconfigured database. Exemplary levels/roles of access include patient and relative level 14a, clinician, case manager and physician access level 14b, agency administrative level 14c, and overall system administration level 14d. By way of example and not limitation, a role or level can be established at log on using passwords, biometric information or any other identification technique without limitation.

Patient and relative or family member level 14a will enable the patient/resident to view a tabular trend screen, a demographic screen, a change password screen, as well as various medically related reports including a tabular trends report, a graphical trends report, as well as a patient information report all without limitation. The clinician role or level 14b, associated with those who are responsible for patient care, such as home health agency employees and the like, provides access to a variety of screens including a current status screen, a tabular trends screen, a patient list screen, an alert limit screen, a demographic screen, standing order screen, change password screen and the like all without limitation. A variety of reports are available at this level including a tabular trends report, a graphical trends report, multi-patient trends report, compliance report, as well as patient information report.

The agency role or level 14c can be associated with a data collection and monitoring agency such as a home health agency. The 14c role or level is responsible for creating and managing various users including various clinicians. The system administration role or level 14d provides access to all available roles for system administration and ongoing management and maintenance of a plurality of systems such as the system 10.

It will be understood that the system 10 can be configured for read-only access. If desired, certain of the roles or levels could be enabled for read and write access. It will be understood, in a disclosed embodiment, that data has been pre-stored.

Figure 1A:
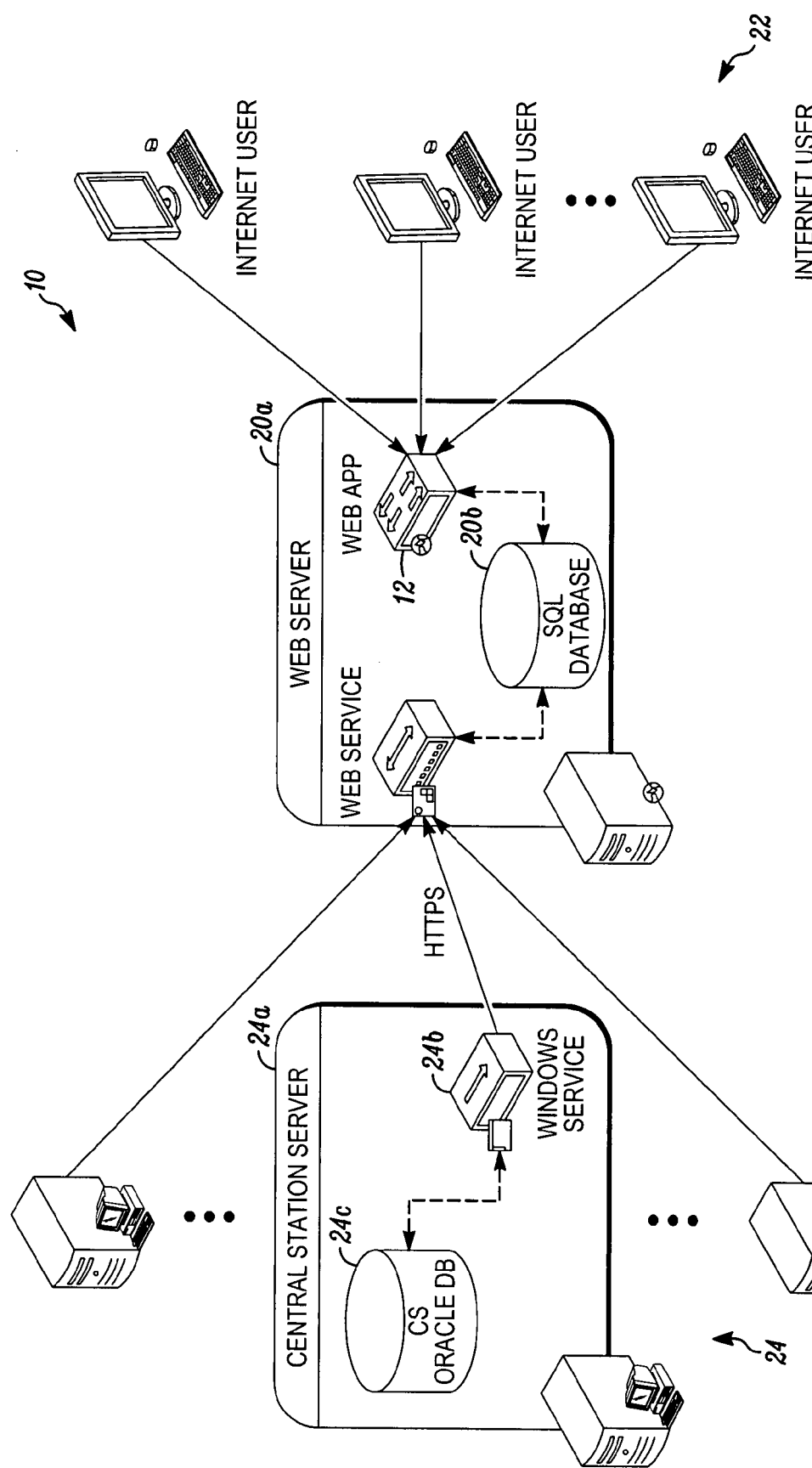
FIG. 1A is a more detailed system view of the system of FIG. 1.

FIG. 1A illustrates additional details of system 10. Web application 12 is illustrated being executed by web server 20a which supports a local patient/resident database 20b. The server 20a provides Internet based services as noted previously relative to the system 10 to individuals operating in various roles indicated generally at 22. These include roles 14a . . . 14d as discussed previously.

In one embodiment, server 20a can be in wired or wireless communication via one or more computer networks with a central station server 24a. The server 24a can communicate via service application 24b and periodically download updated patient/resident medically related data from a database 24c to the server 20a and associated database 20b.

Those of skill will understand that the configuration of the system 10 (illustrated in FIG. 1A) is exemplary only and other embodiments come within the spirit and scope of the present invention. It will also be understood that the particular form of the implementation of the web application 12 is not a limitation of the present invention.

FIGS. 2-5 illustrate exemplary flow as well as information as to screens available to each of the roles/levels 14a . . . 14d.

Figures 2, 3:
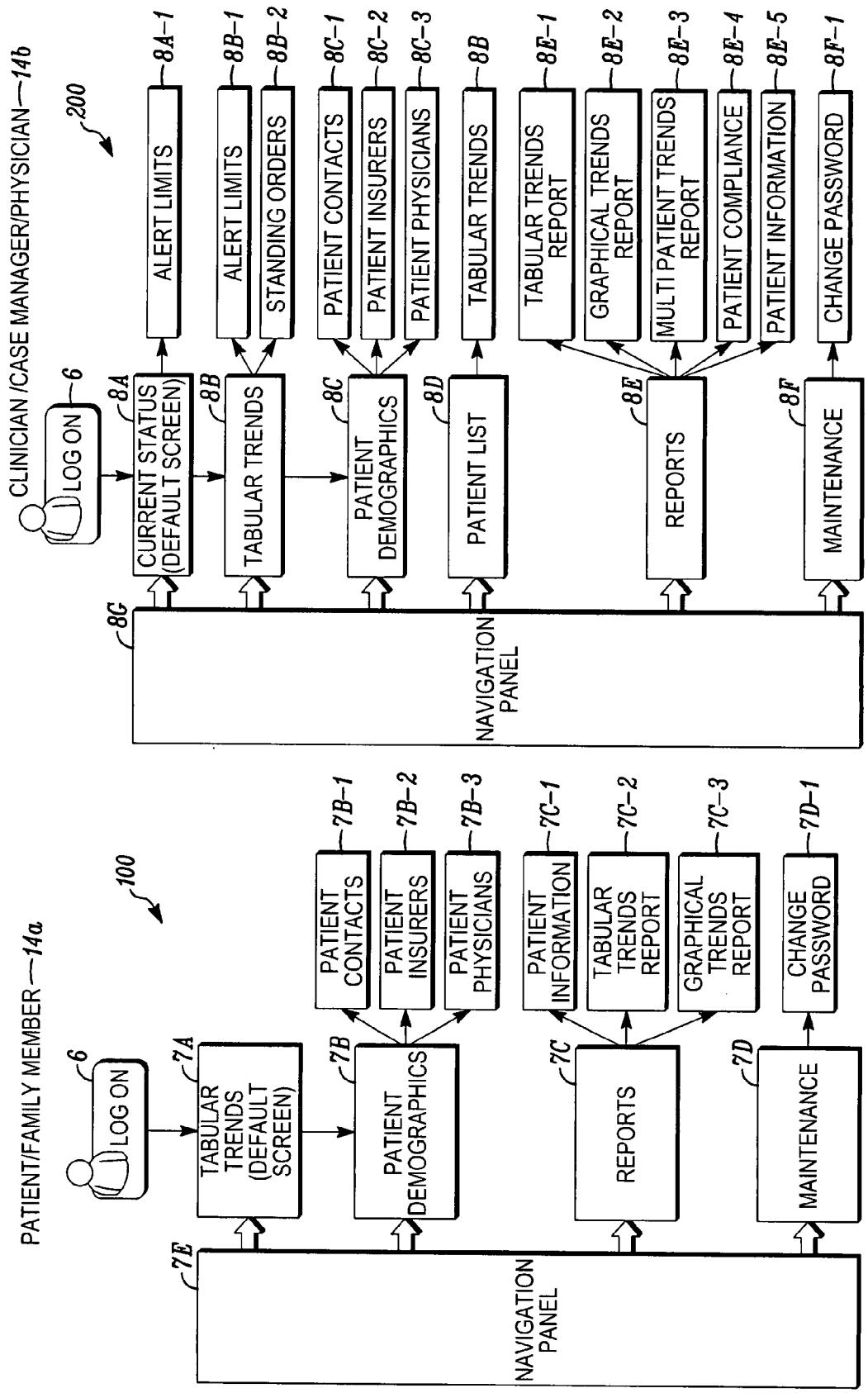
FIG. 2 illustrates information availability at a first access level.
FIG. 3 illustrates information availability at a second access level.

As illustrated in FIG. 2 for role/level 14a process 100 is available enabling the patient/resident or relative to access the database 20b via a variety of screens and obtain different reports.

Figure 6:
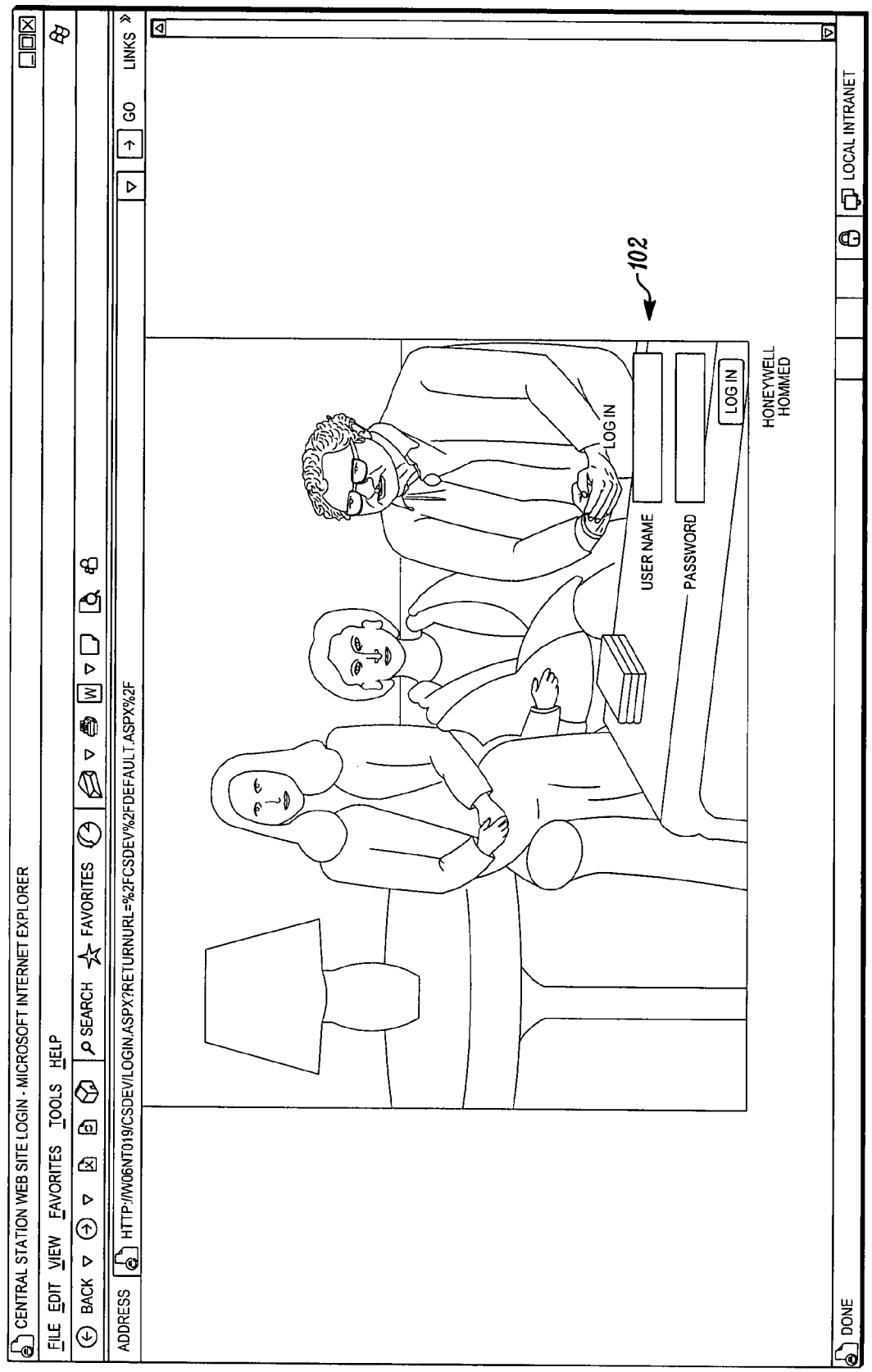
FIG. 6 illustrates an exemplary sign on screen.

To establish an access level or a role, when an individually initiates interaction with the application 12, a log on screen, for example as illustrated in FIG. 6, is presented. The log on screen provides a region 102 where a user name and password can be entered. For example for patient/resident Carl Banks, at various levels/roles as explained below.

As noted above, alternate forms of identification can be used in addition to or instead of passwords. FIGS. 7A-7D illustrate role/level 14a access.

Where log on has been successful, a tabular trends default screen of FIG. 7a is presented. The default screen can include a navigation panel 7E which enables the user to select among various available screens and reports. The tabular trends screen of FIG. 7a presents various patient/resident trend information indicated generally at 104.

Figure 7B:
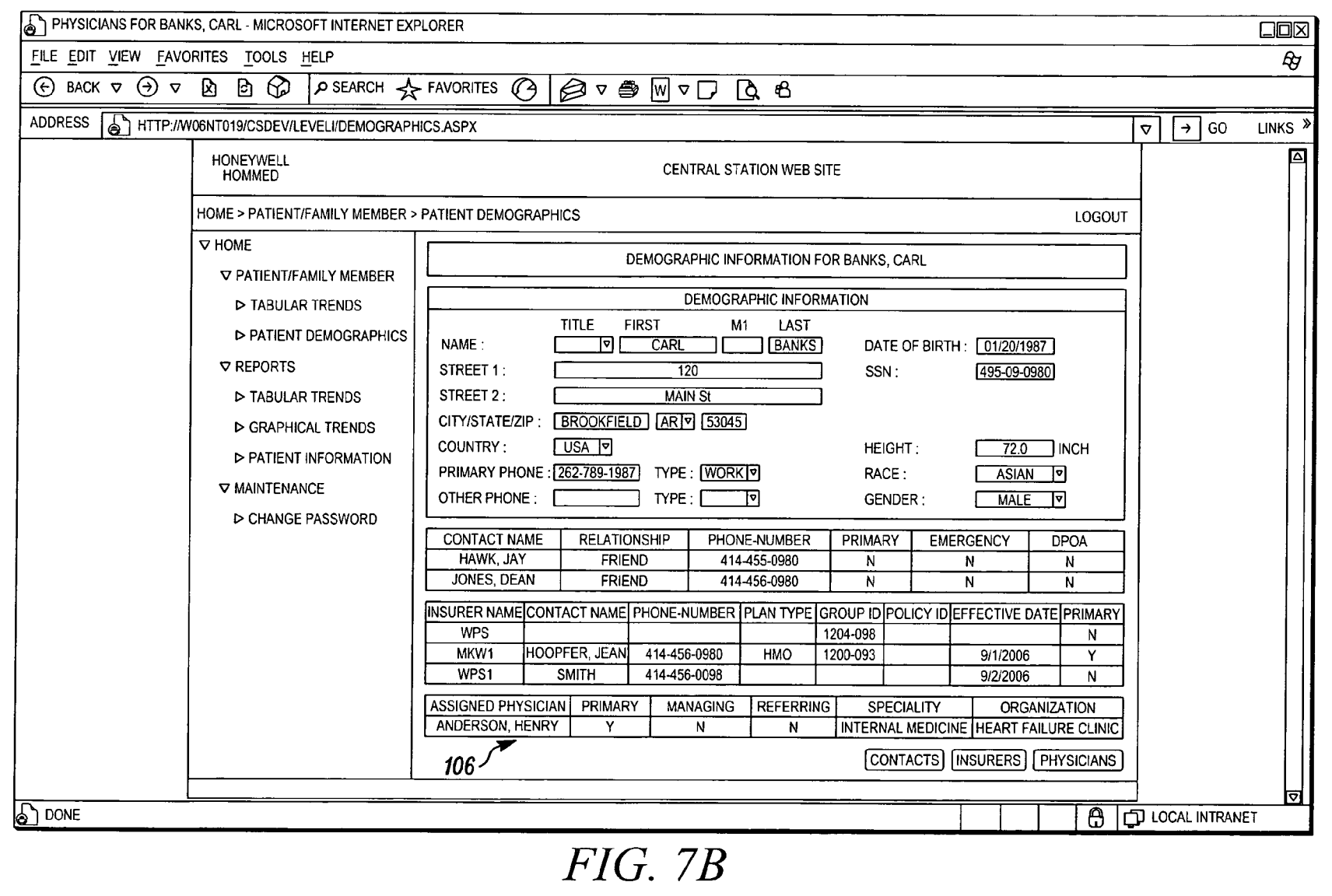
Figure 7B-1:
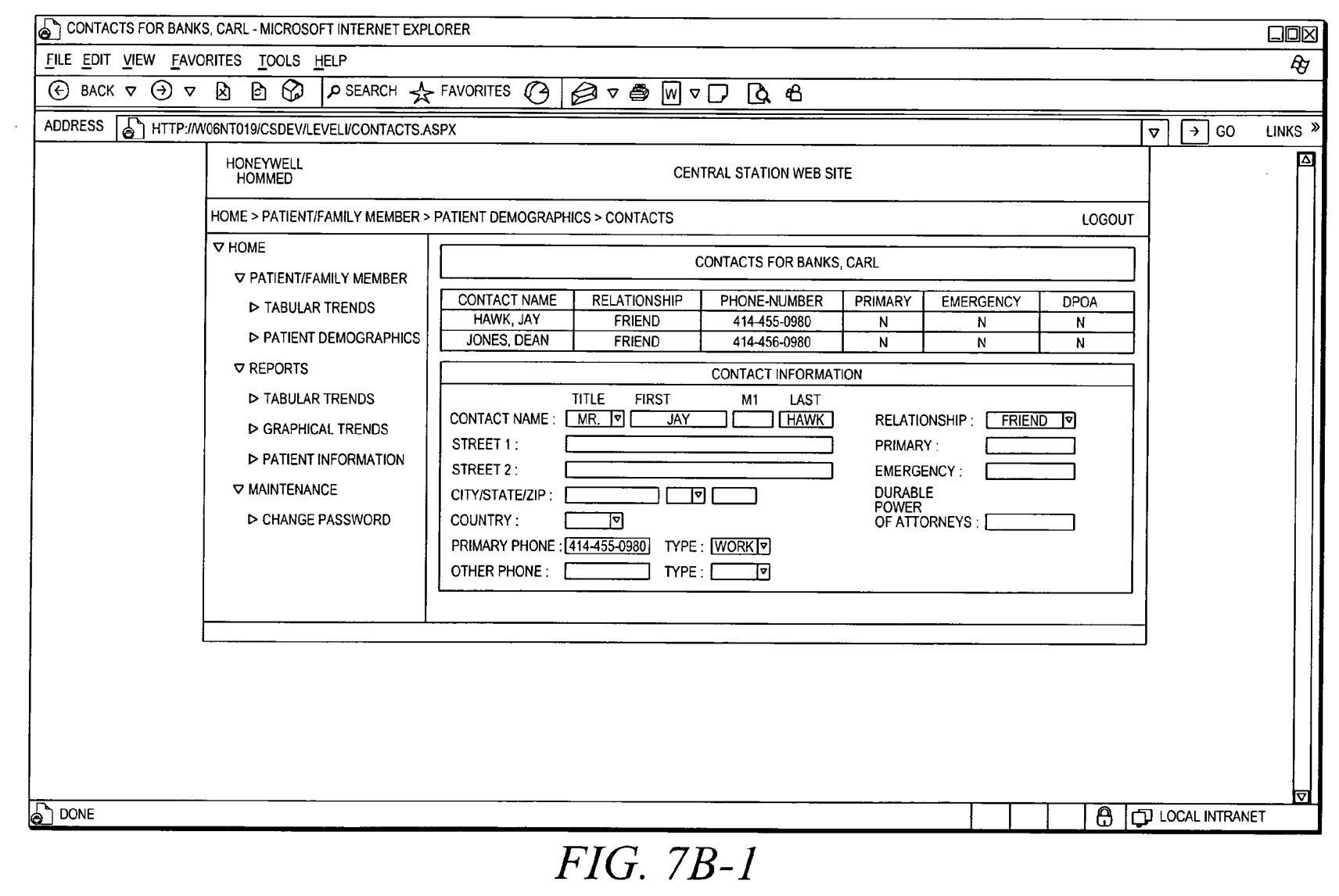
Figure 7B-2:
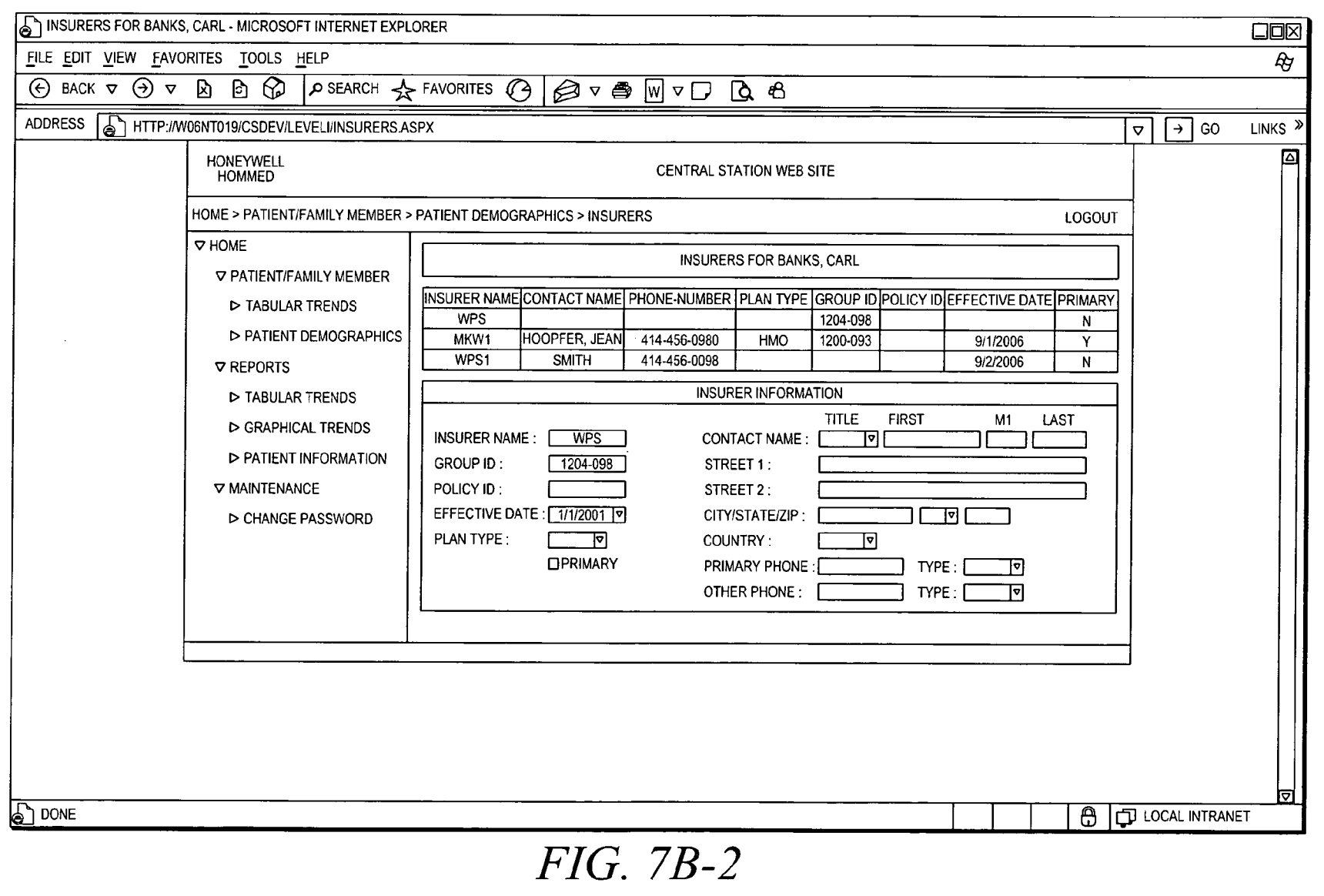
Figure 7B-3:
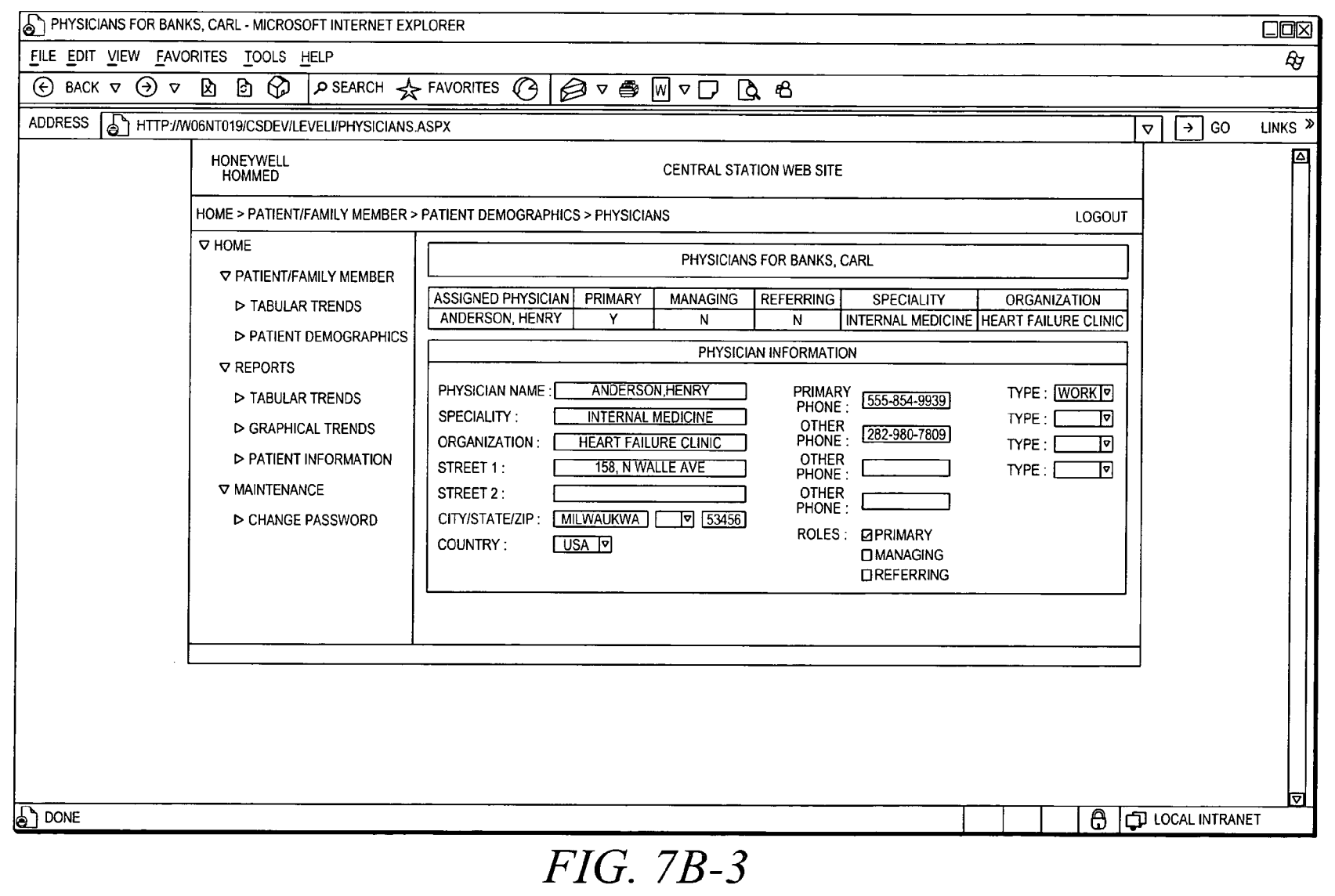
Figure 7C-2:
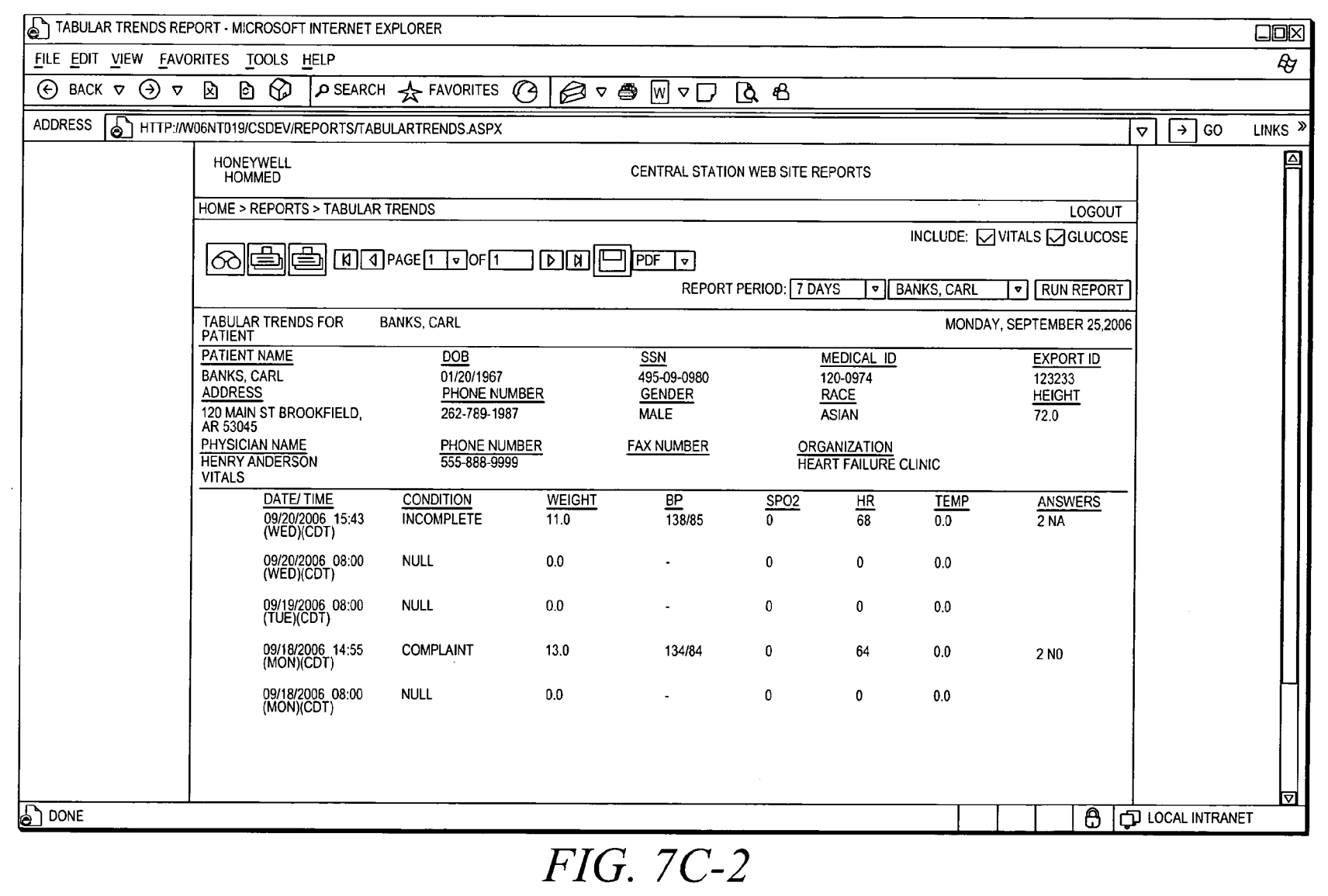
Figure 7C-3:
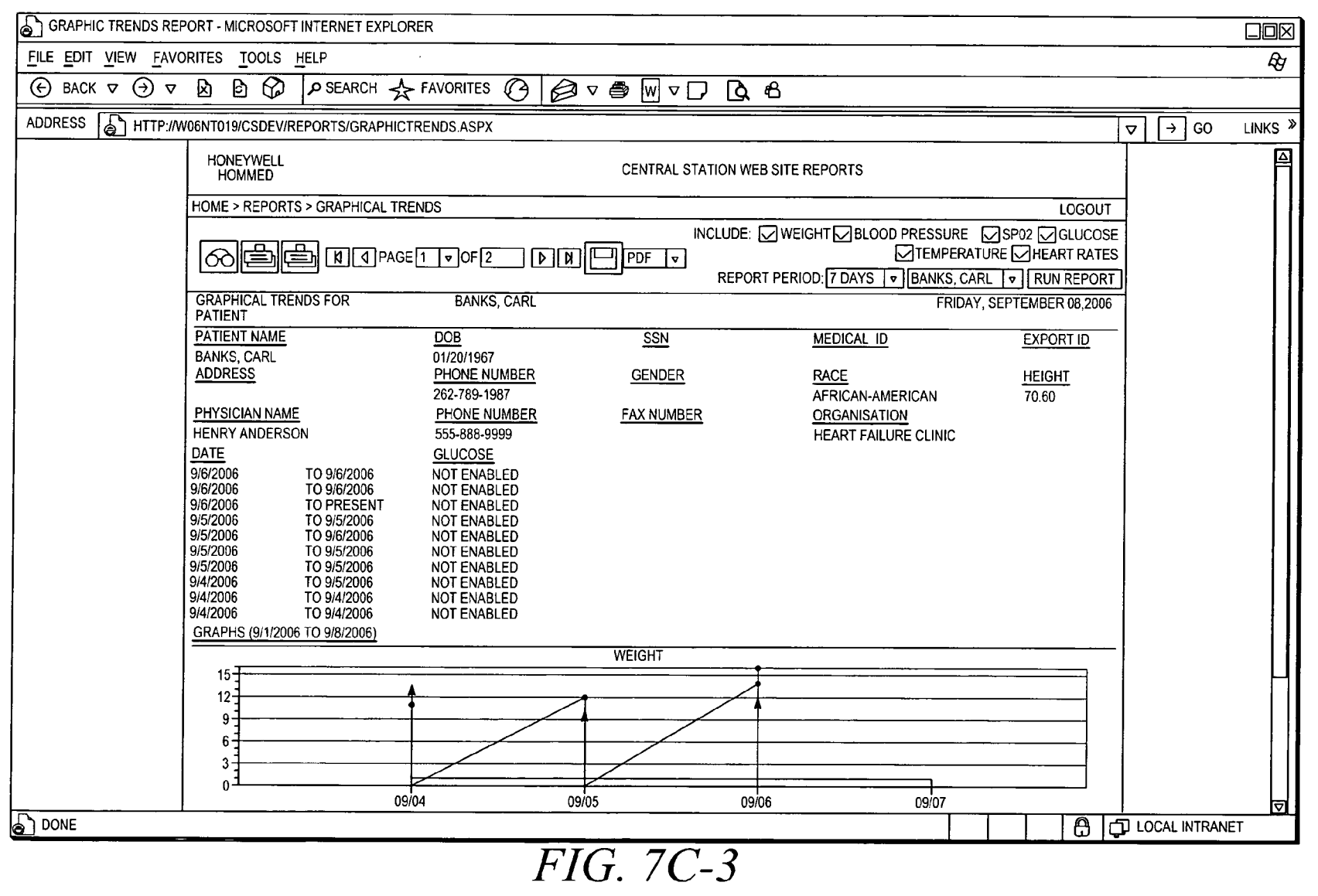

A patient demographic screen of FIG. 7B can be selected. The screen of FIG. 7B presents overall patient demographic information indicated generally at 106. Subscreens for patient contacts, FIG. 7B-1, patient insurers, FIG. 7B-2 or patient physicians, FIG. 7B-3 can be selected for display. Each presents respective associated information. As an aspect of the current level, namely 14a, the information presented on screens 7A, 7B, as well as subscreens 7B-1 . . . 7B-3 is a subset based on the current role/level.

Additionally, a report function 7C can be selected. Various reports such as a patient information report can be displayed, see FIG. 7C-1. A tabular trends report, FIG. 7C-2 and a graphical trends report can be displayed, see FIG. 7C-3 and/or printed.

Figure 7D:
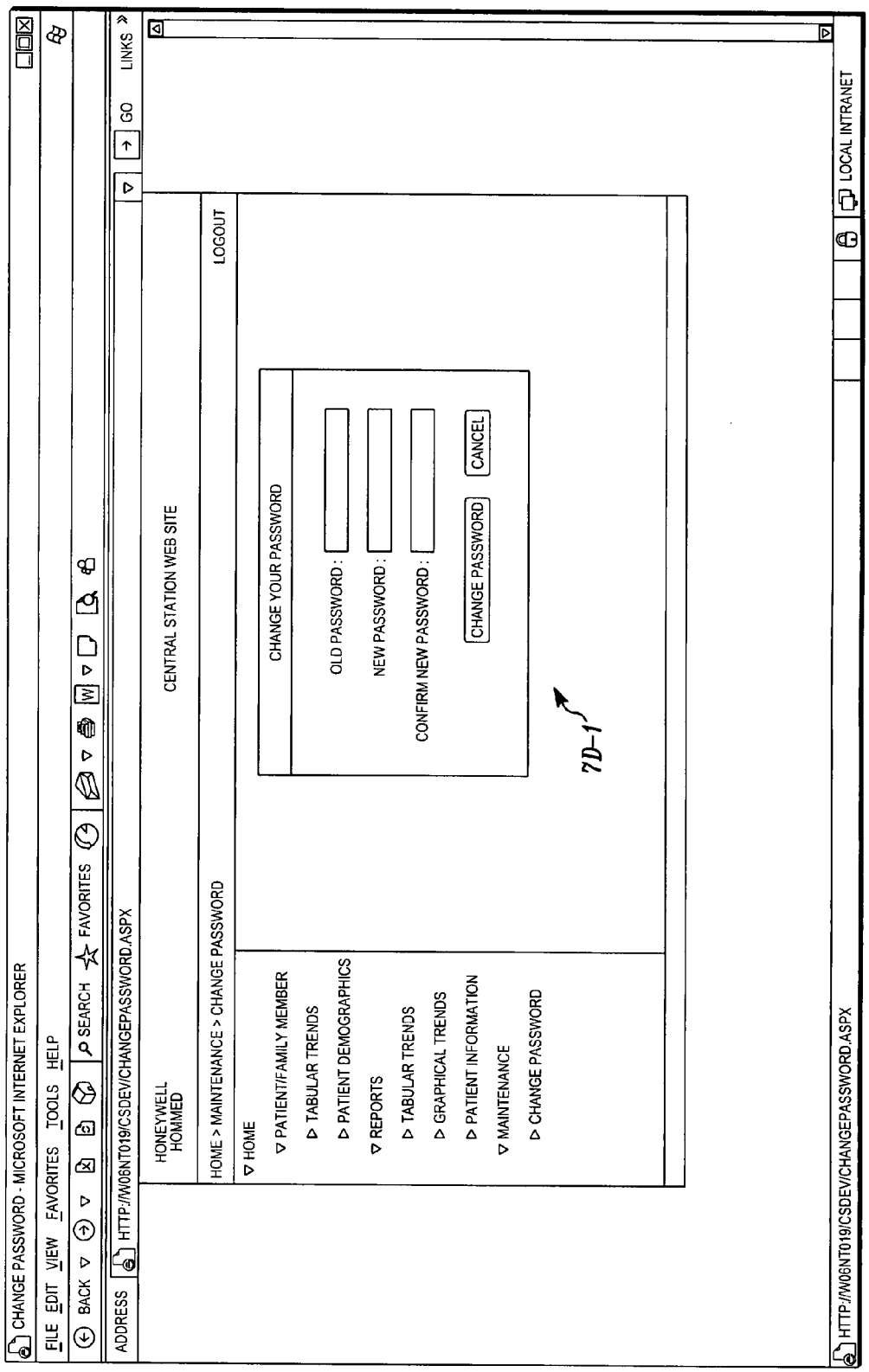
FIG. 7D illustrates an exemplary password changing screen usable with the system of FIG. 1.

A maintenance function 7D can be selected which at the 14a level can include changing a password as illustrated in FIG. 7D-1.

Relative to the clinician level 14*b* a process 200 can be executed which can provide additional information not available at the 14*a* level. FIGS. 8A-8F illustrate role/level 14*b* access.

Figure 8A:
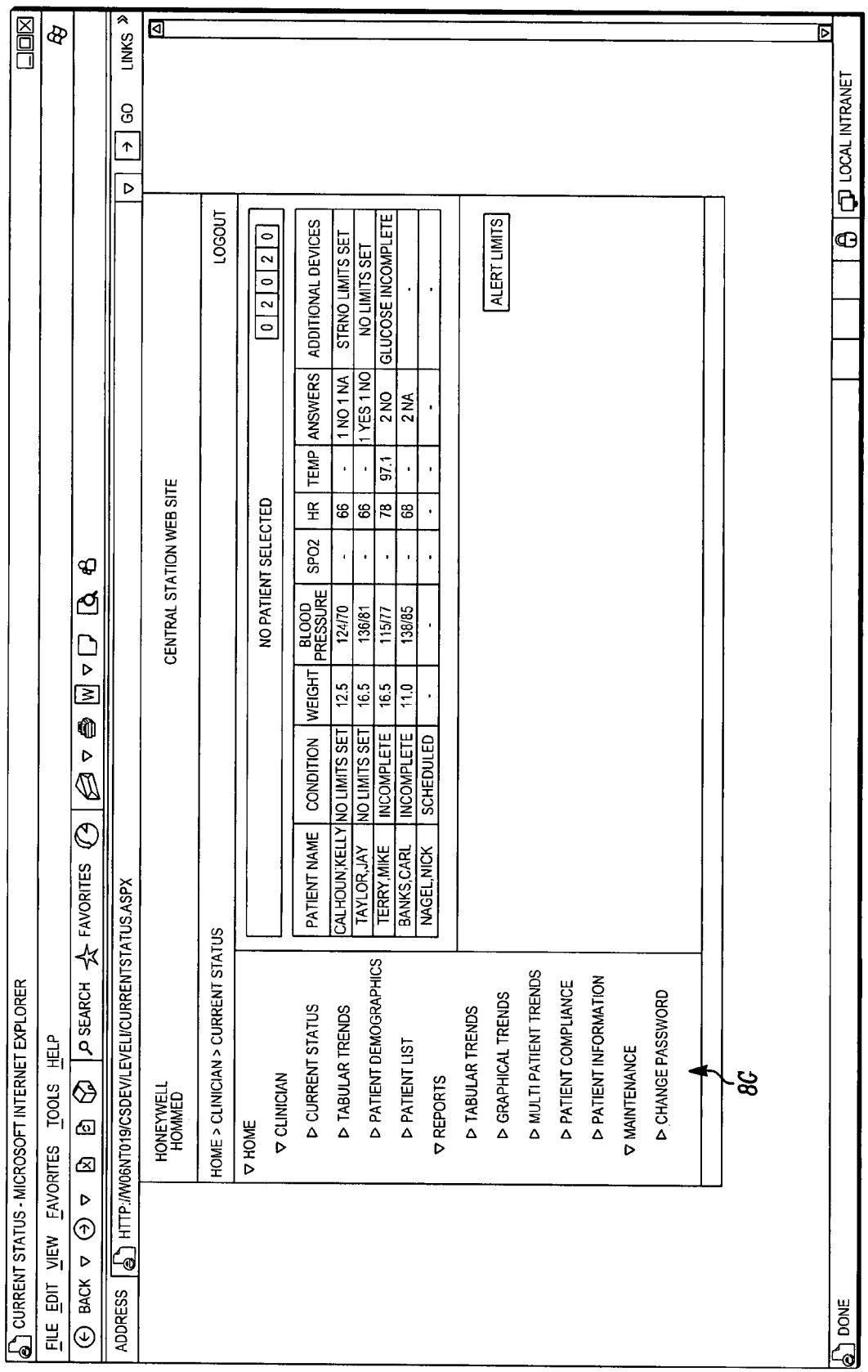
FIG. 8A is an exemplary status screen in accordance with the present invention for a clinician access level.
Figures 1, 8A:
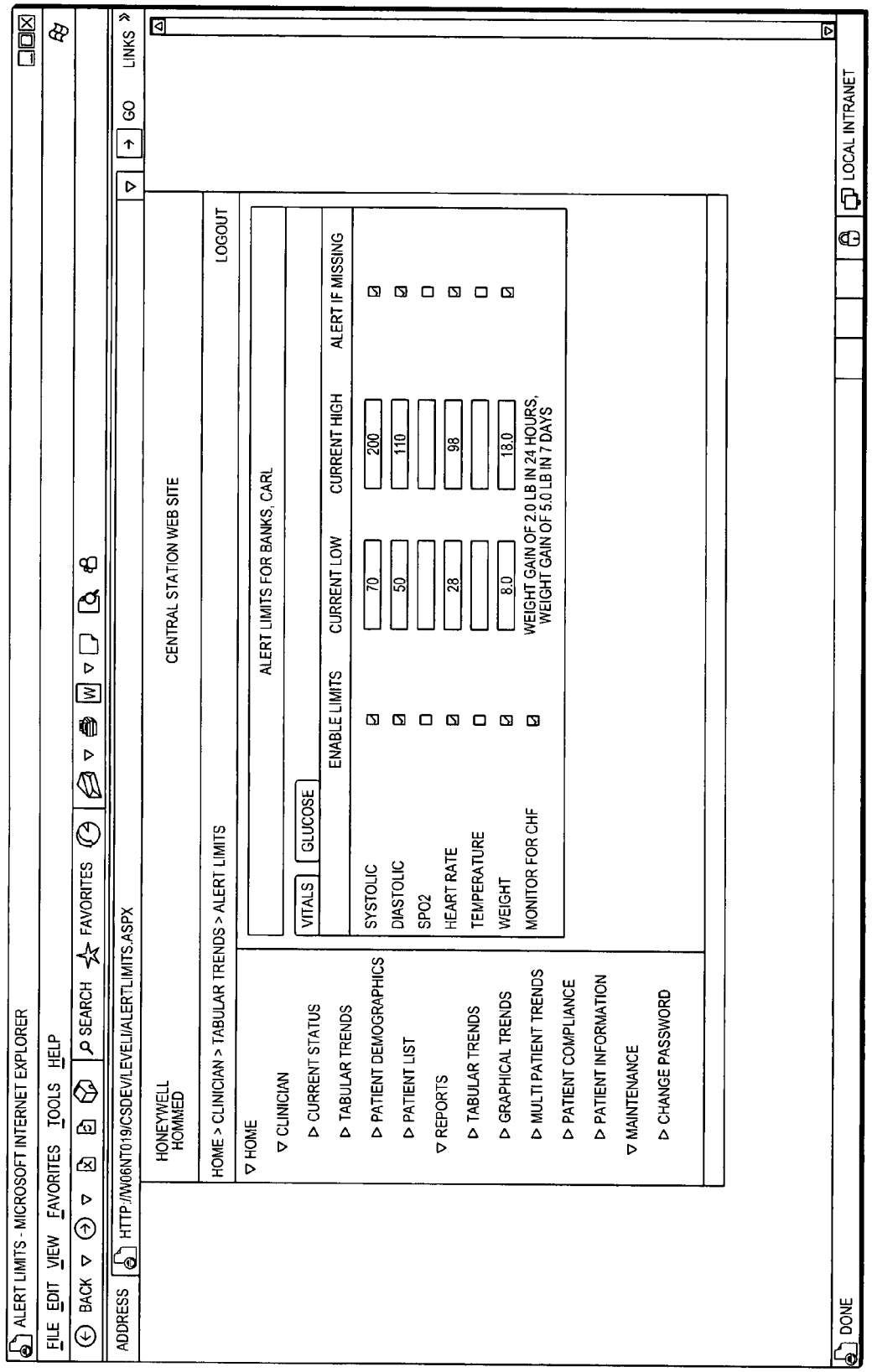
Figures 1, 8B:
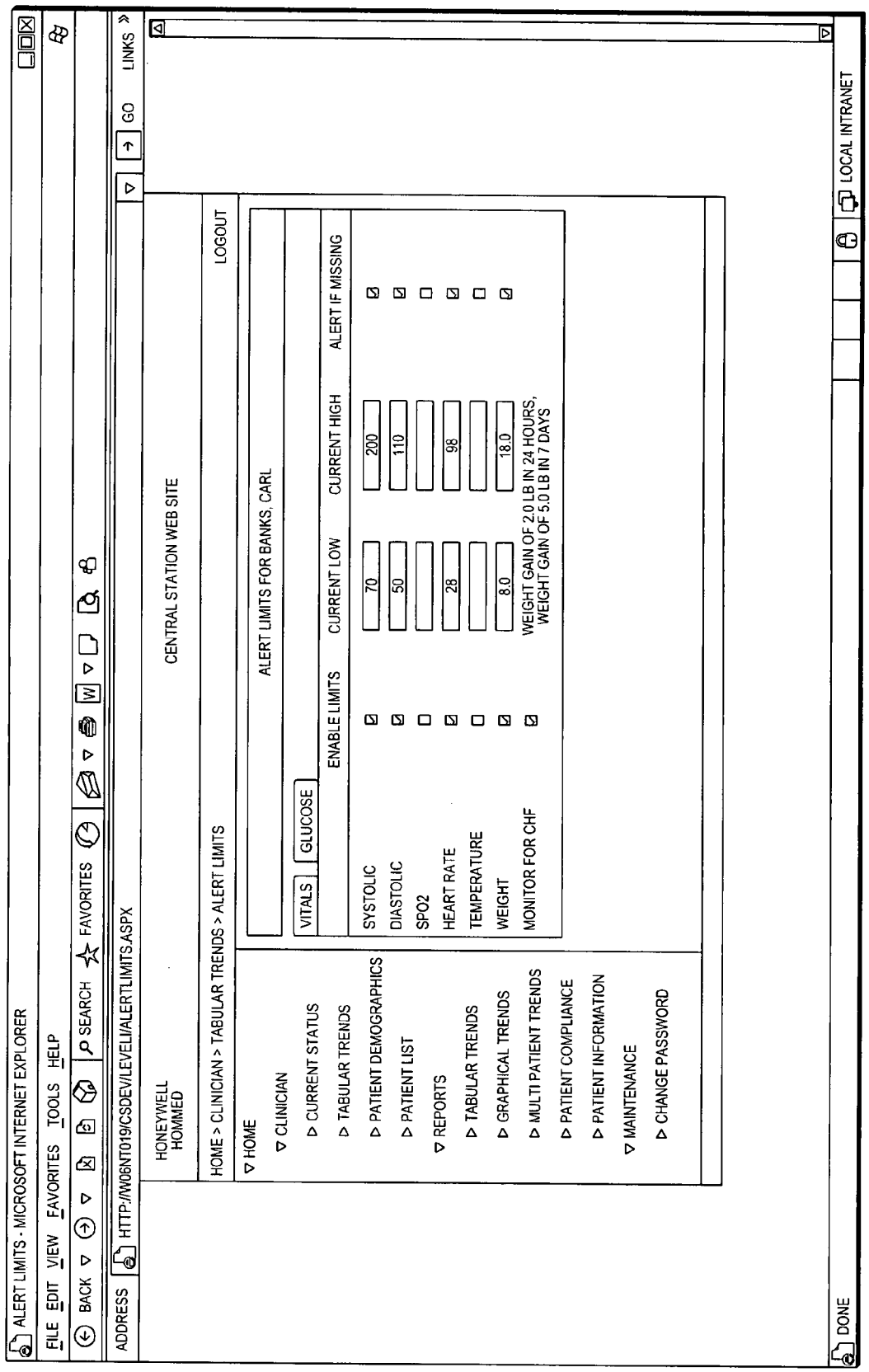
FIG. 8B is an exemplary screen illustrating tabular trends of a selected individual.
Figures 2, 8B:
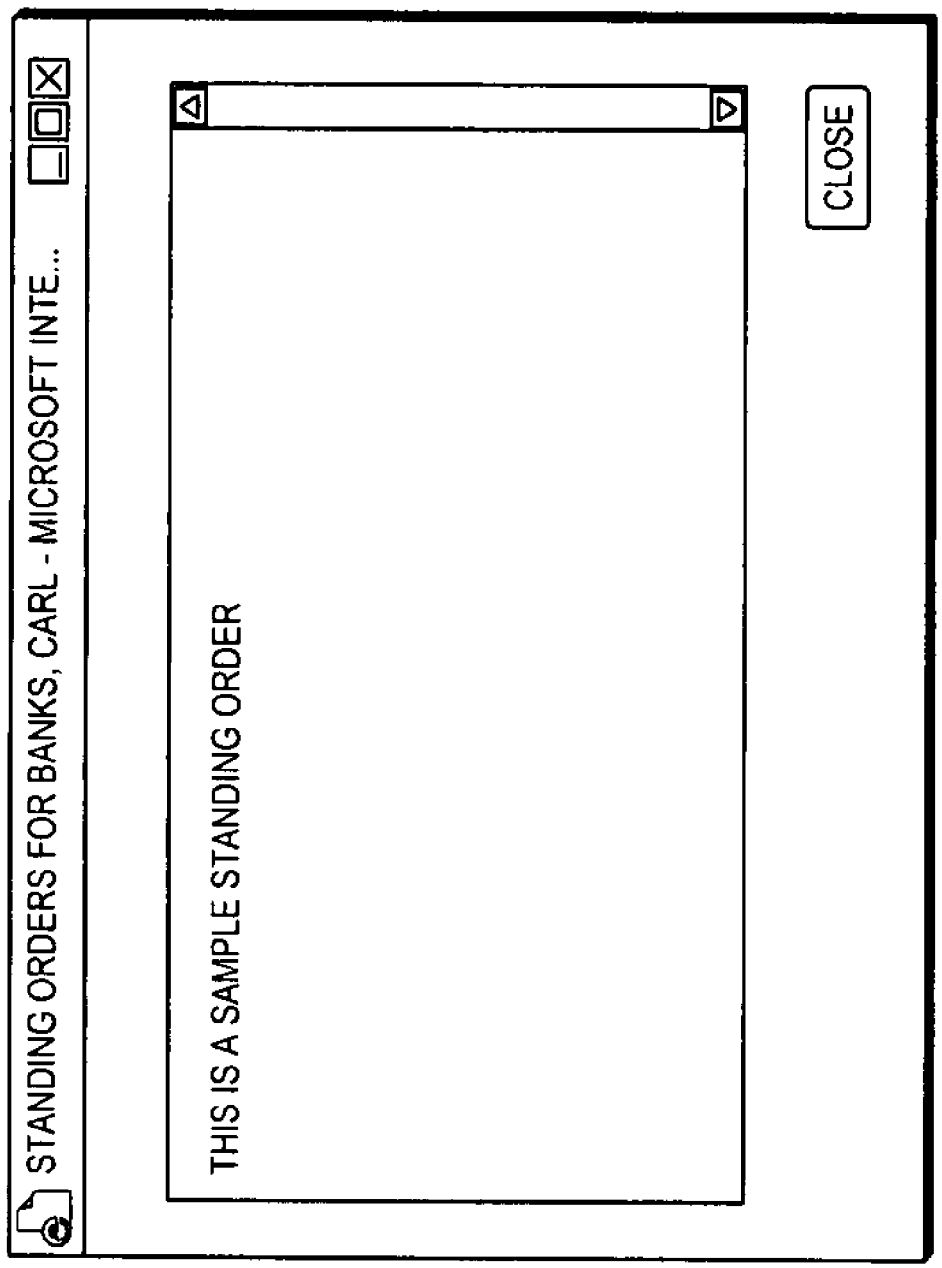

Relative to the process 200 assuming that log on at the 14*b* level has been successful, current status information for a variety of patients/residents can be presented, see FIG. 8A. A patient can be selected and alert limits information viewed as illustrated in FIG. 8A-1. Additionally, a navigation panel function 8*g* is available to select among presentable data as well as reports. Tabular trends function 8*b* can be selected and trend information displayed for the respective patient/resident as illustrated in FIG. 8B. Alert limit information and standing order information can be selected and presented as illustrated in FIGS. 8B-1, 8B-2 for the respective individual.

Figure 8C:
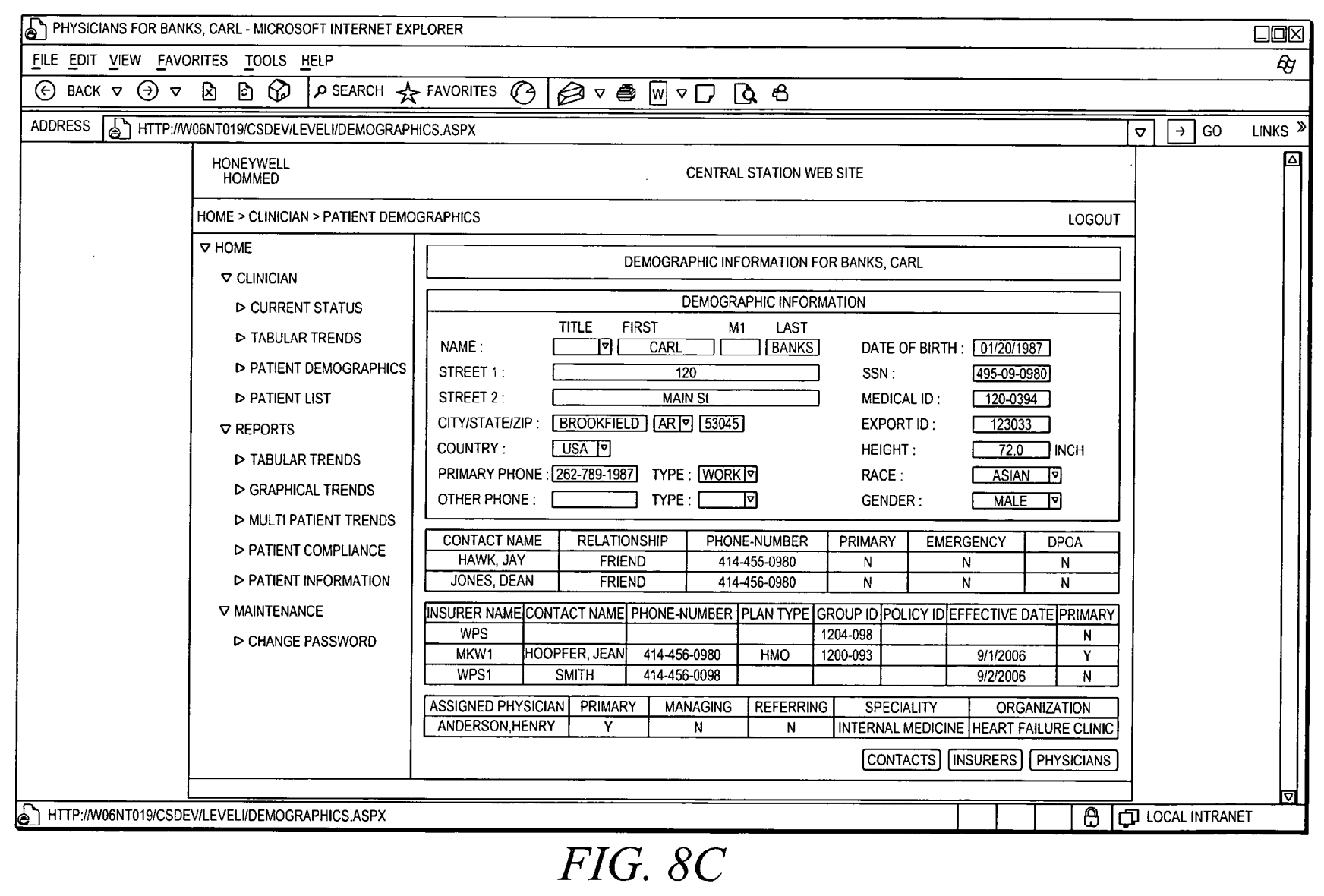
Figure 8C-1:
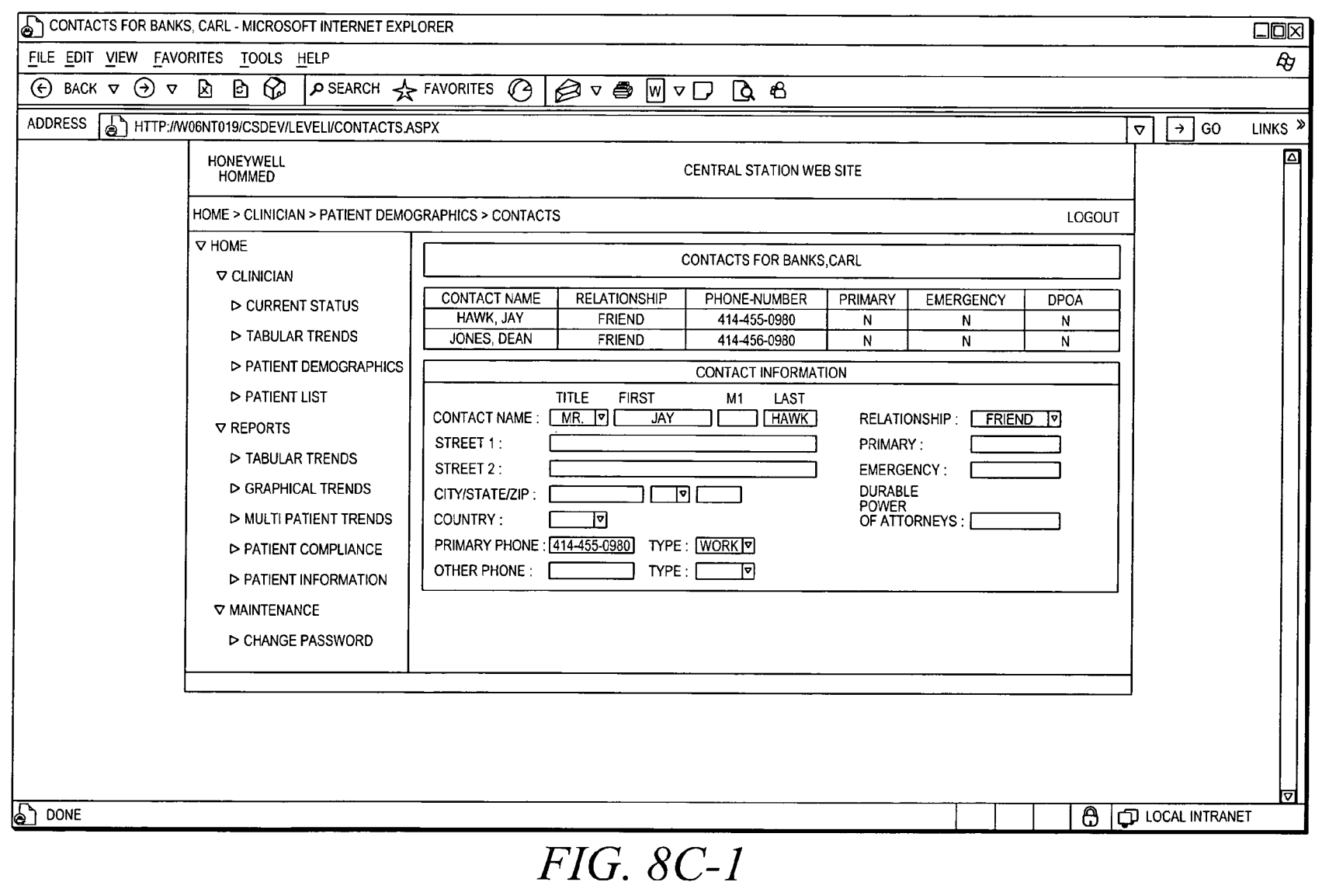
Figure 8C-2:
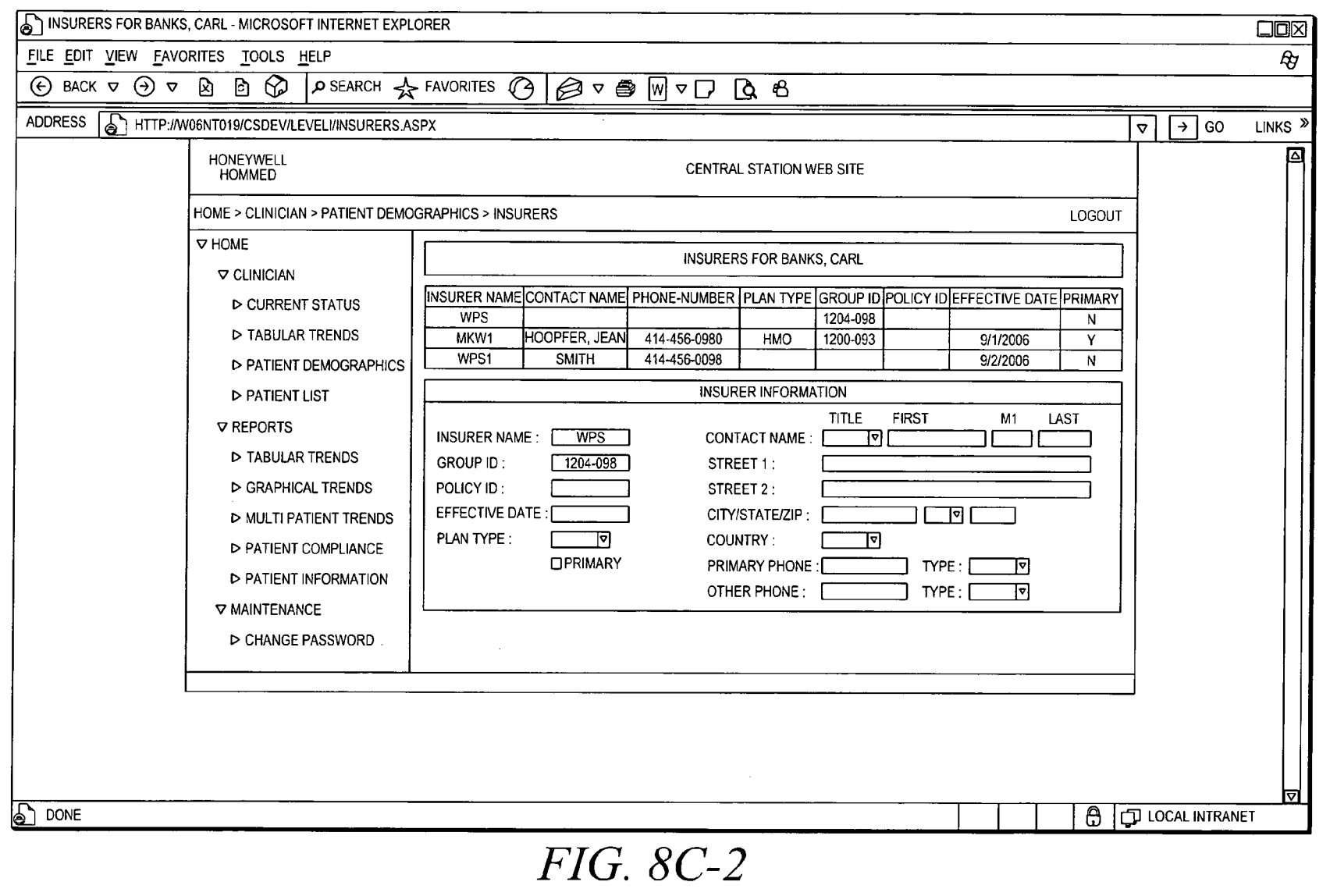
Figure 8C-3:
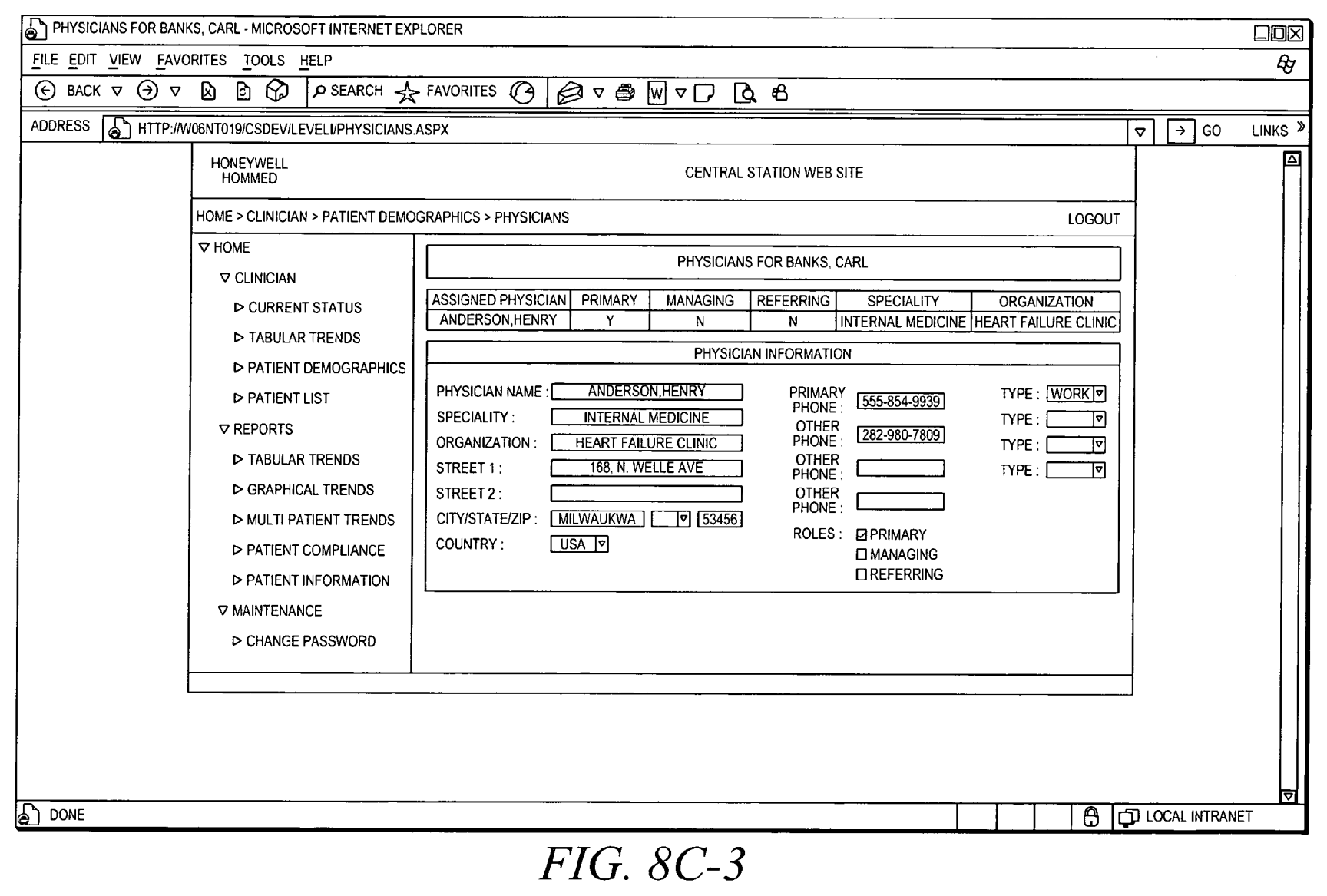
Figure 8E-2:
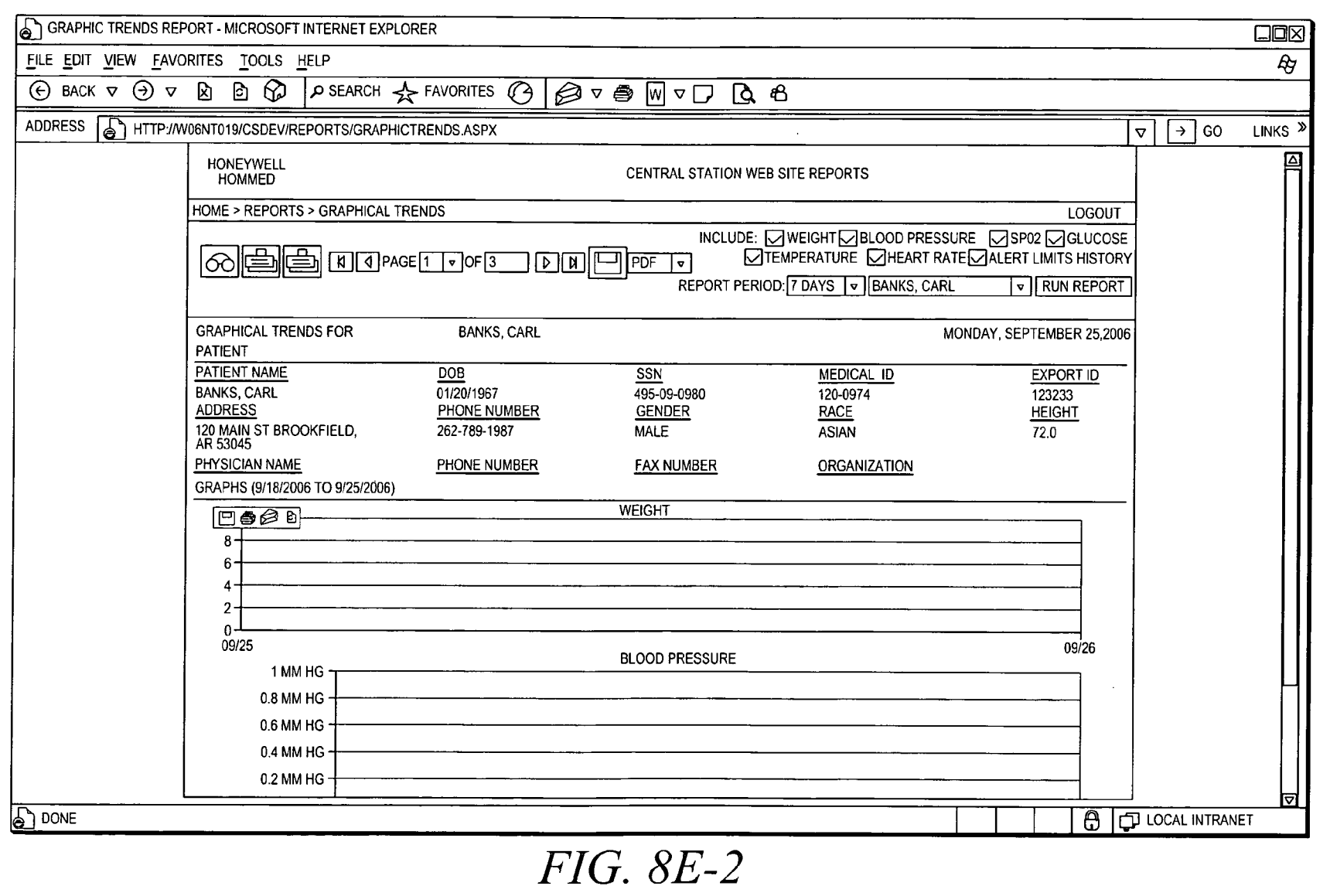

Patient demographics information can be selected and presented for review as in FIG. 8C for the respective individual. Patient contact information, insurance information as well as physician information can be selected and displayed as in FIGS. 8C-1, -2, and -3.

A patient list can be selected and displayed, see FIG. 8D. For a selected patient/resident, tabular trends can be selected and displayed as in FIG. 8B. Those of skill will understand that data in the figures such as FIG. 8B can be color coded (green, yellow, red) to attract attention.

Reports 8*e* can be selected. A tabular trends report can be presented, FIG. 8E-1, a graphical trends, report can be selected and displayed, see FIG. 8E-2. Multi-patient trends report, FIG. 8E-3, patient compliance report, FIG. 8E-4 or patient information reports, FIG. 8E-5 can be selected, displayed and printed as required. A maintenance function 8*f* can be selected, and as in FIG. 8F the user's password can be changed on a region of the screen indicated generally at 8*f*-1.

Figure 4:
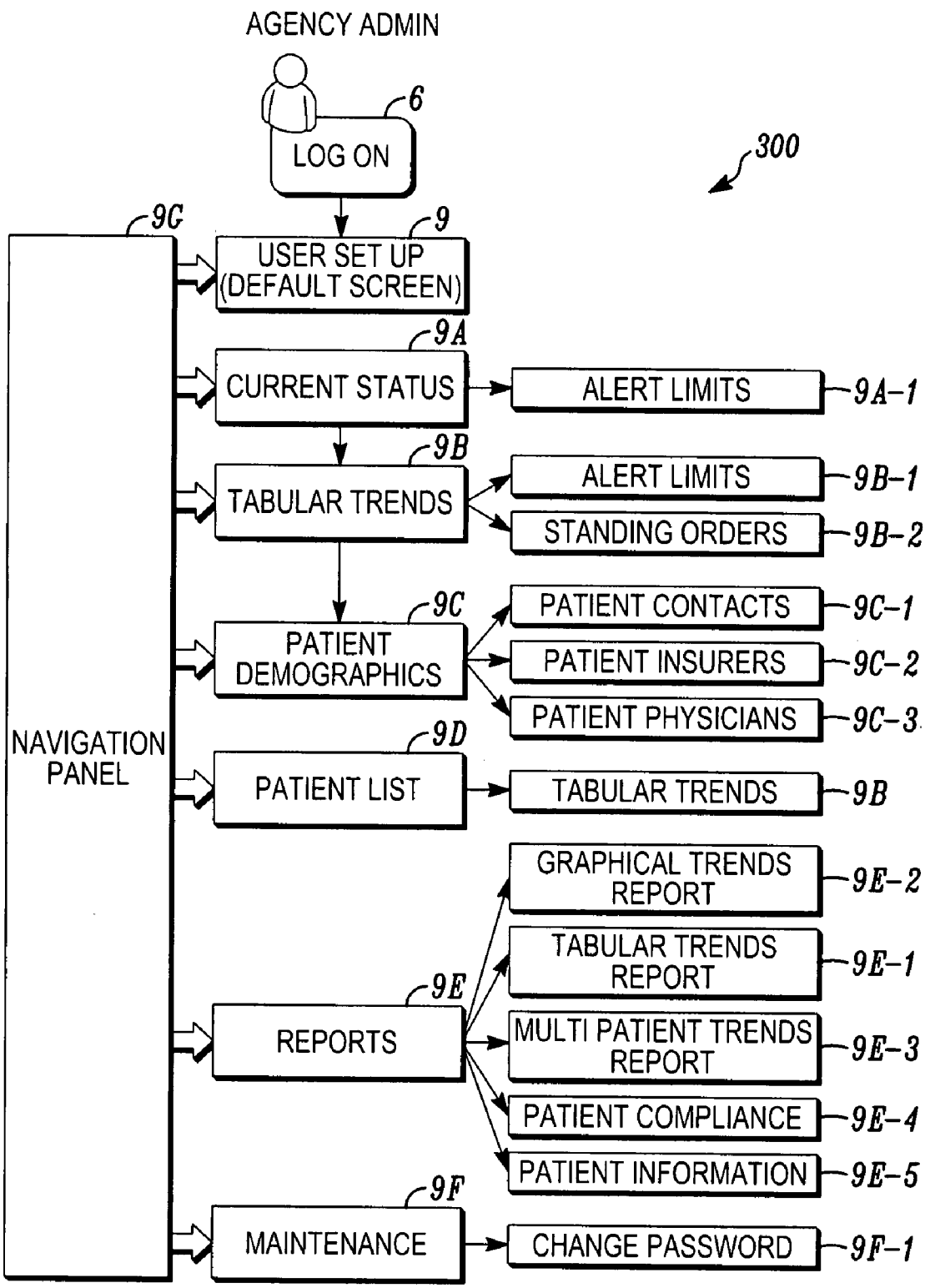
FIG. 4 is a diagram which illustrates information availability at a third access level.

Relative to FIG. 4 and process 300, if the log on process identifies the individual as having an agency administrative role or function 14*c,* access is then provided via the control software of the web application 12 to process 300. A user setup screen 9 is initially presented with a navigation panel 9G. A variety of functions and reports can be selected. A current status screen 9A can be presented, comparable to the screen of FIG. 8A, which identifies a plurality of patients who can be selected. Alarm limits 9A-1 can be selected for a particular patient or resident and an alarm limit display, comparable to that of FIG. 8A-1 can be presented.

Where a tabular trends function 9B has been selected, an informational display comparable to that of FIG. 8B can be presented. Alarm limits 9*b*-1 and standing orders 9*b*-2 can be selected and in response thereto displays comparable to those of FIGS. 8B-1 and 8B-2 can be presented to the user.

Patient demographic information 9*c* can be selected. When so selected, a display of patient demographics comparable to that of FIG. 8C can be displayed for the user. Patient contacts, insurers as well as physicians can be selected for display 9C-1, -2 and -3 comparable to the displays of FIGS. 8C-1, 8C-2 and 8C-3.

Where a patient list function 9*d* has been selected a display comparable to that of FIG. 8D can be presented to the user identifying various patients. Tabular trends 9*b* can be selected for review relative to a specific patient/resident. A report function 9*e* can be selected which will provide one or more displays which can be printed as reports, including a tabular trends report 9*d*-1, a graphical trends report 9*e*-2, a multi-patient trends report 9*e*-3, a patient compliance report 9*e*-4, and a patient information report 9*e*-5. These respective reports can be presented in a format comparable to those of the reports of 8*d*-1 . . . 8*d*-5.

Figure 8F:
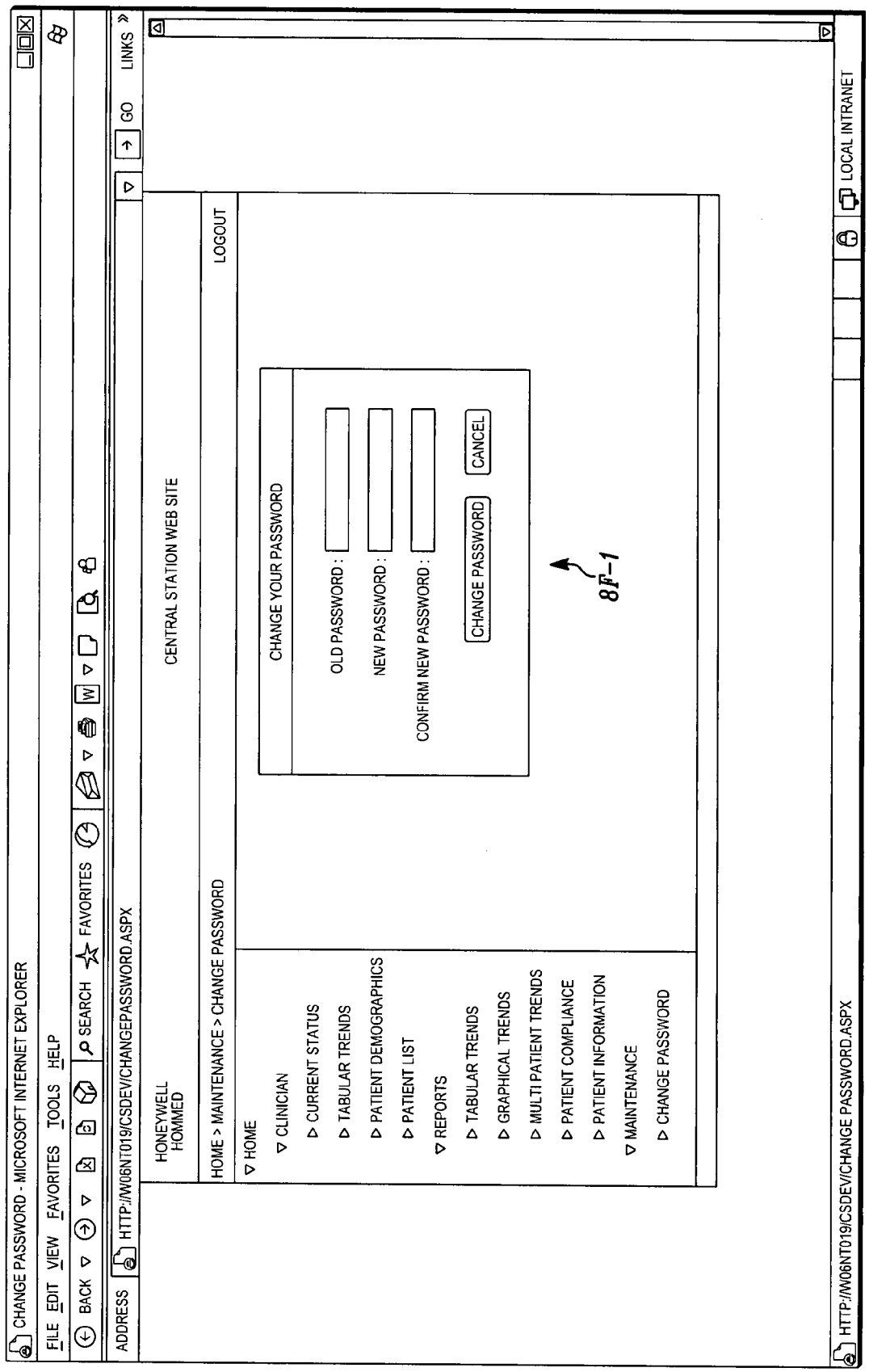
FIG. 8F is a maintenance screen for changing an individual's password.
Figure 9A:
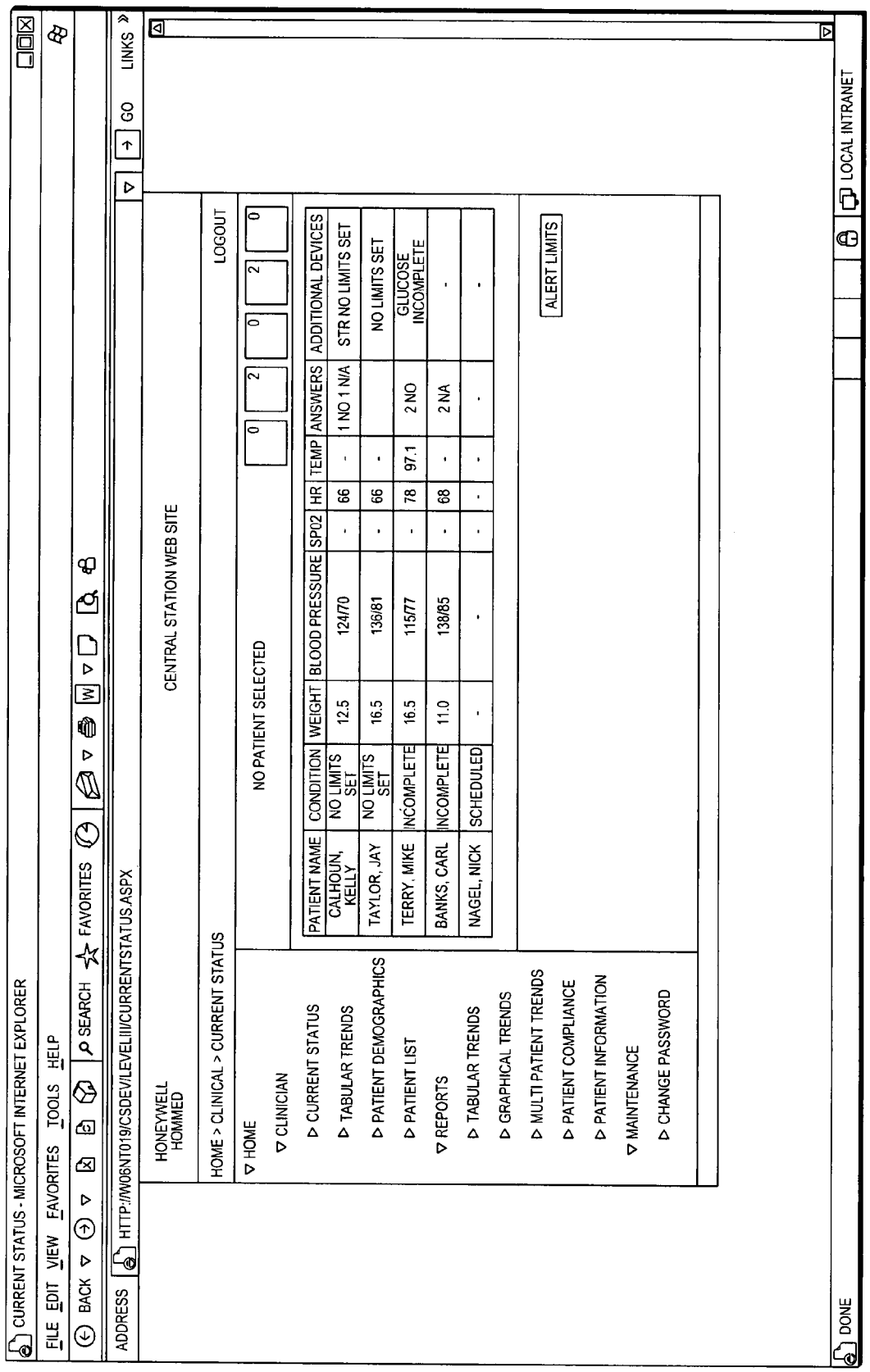
FIG. 9A is an agency level current status screen.

A maintenance function 9*f* can be selected such that the user can change his or her password via display 9*f*-1 comparable to the display of FIG. 8F-1.

As noted above, the agency administrative level or role can include creating and managing the various users via user setup screen 9, with respect to the organization with which he/she is working. This level can also have access to various user reports, an agency specific system log, an audit log and other user reports. Such agencies also carry on clinical functions of the level 14*b* role.

Figure 5:
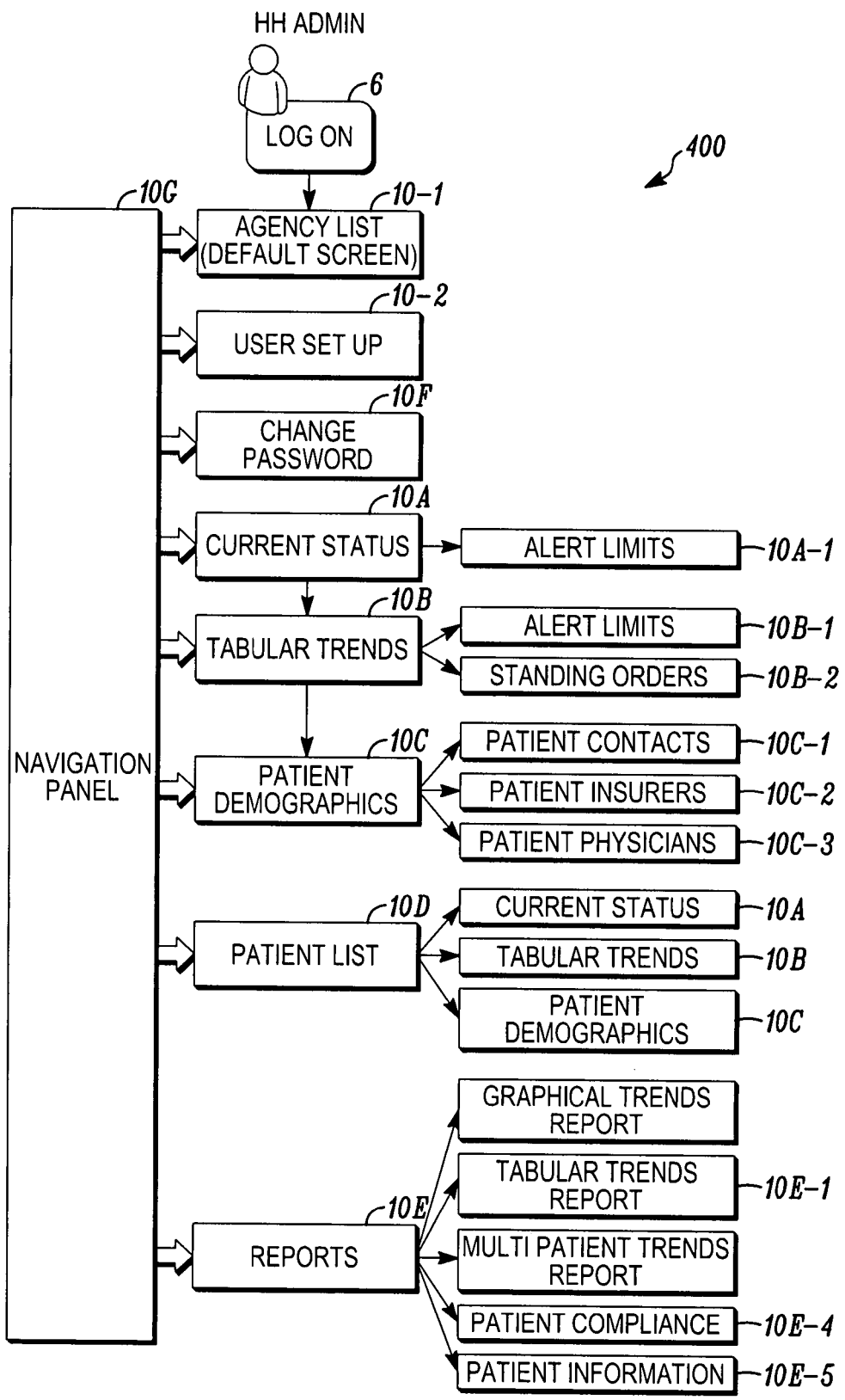
FIG. 5 is a diagram which illustrates information availability at yet another access level.

FIG. 5 illustrates a process 400 available to system administrators at the 14*d* level. This level can be provided access to patient and administrator functions across a plurality of agency implemented systems comparable to the system 10.

As illustrated in FIG. 5 in the process 400, after a successful log on an agency list screen FIG. 10-1 is presented. The screen identifies various agencies and presents information of a type that the system administrator would find useful. The agency list screen also presents a navigation panel 10*g* whereat the user can select various other functions and reports to be presented. A user setup screen FIG. 10-2 can be presented which enables the system administrator to establish and/or modify various agency characteristics. The system administrator also has access to current status of patient/resident 10*a* via a screen comparable to that of FIG. 8A. Alarm or alert limits can be selected for display relative to a respective patient/resident 10*a*-1 as illustrated on the screen of FIG. 8A-1.

Tabular trends 10*b* can be selected via the navigation panel 10*g* and a display comparable to FIG. 8B can be presented for the user. Alarm or alert limits or standing orders 10*b*-1, 10*b*-2 can be selected and displayed as in FIGS. 8B-1, 8B-2.

Patient demographics can be selected for display 10*c* and information presented as to demographics as in FIG. 8C. Additionally, patient contacts, insurers and/or physicians can be selected 10*c*-1, -2, -3 and such information presented on screens comparable to those of FIGS. 8C-1, -2 and -3.

Patient identification information via patient list 10*d* can be displayed for various agencies as illustrated in FIG. 10-3. Status, trend and demographic information can be selected and displayed for respective patients/residents. A report function 10*e* can be selected. Various reports such as a tabular trends report 10*e*-1, graphical trends report 10*e*-2, a multi-patient trends report 10*e*-3, patient compliance report 10*e*-4, and patient information report 10*e*-5 can be presented for the user in formats as illustrated in FIGS. 10-4 . . . -8.

For maintenance purposes, a change password function 10*f* can be selected and the password changed in accordance with a screen of the general type as in FIG. 8F.

Thus, in summary, differing displays which provide access to differing levels of date or information can be presented in accordance with a selected role/level such as 14*a* . . . 14*d*. Optionally, selective roles could also support writing additional data into the database for a respective resident/patient.

It will also be understood that the above discussion is only exemplary. Embodiments of the invention are not limited to medically-related information or data. Security features including encryption and the like can be incorporated to protect privacy of the data, and that of the respective patient/resident.

As noted above, the data that is graphically presented can be expected to vary between roles. Additional variations follow. The patient demographics main screen is different for the patient/family member access vs. the other roles. This one does not include Export ID and Medical ID due to the sensitive nature of this information.

In addition, the Agency Administration allows view access of the Organization, but the System Administrator role allows the modification of the Organization. The patient/family member reports greatly differ from that of the other roles. Each of these reports does not include Alert limits information. Also, the Tabular Trends screen, as in FIG. 7A, differs greatly for the patient/family member role—colors and alerts are not included as they are in other roles, as in FIG. 8B.

Embodiments of the invention can also include:

All vitals information available on the web application 12 can be incorporated into customized reports by role that can be printed out. This allows for print outs of vitals and other relevant care information from the web application by role.

Due to the having the basic vitals information in the central station 24 and the web application 12 there is some built in redundancy. The redundancy does not include all information, which is a benefit, because there is minimized exposure to patient sensitive information by the limited access to the larger database 24c where security concerns are more significant.

The application of color to the severity of the parameter condition breaks provides an ability to triage the status of the patients' information to determine the priority for review on the web for clinical and agency administrative roles is an independent claim.

Other aspects of the invention can include:

Method of using the web for a private pay program utilizing the patient family member role;

Role based web access to patient vitals and other information necessary to monitor patient health;

Web access to physical therapy information including pain scale and other occupational therapy devices, programs, instructions, education;

Web role based access architecture;

Skin-able screens by agency by role;

Physician role based access that allows subgroups access to patient information across agency boundaries with partner distribution channel;

Start and Stop/Timer for billing care giver time for accessing patient information;

Tracking time spent by patient and/or by role for billing purposes;

Print outs of vitals and other relevant care information form the web by role;

Acknowledge of vitals over the web;

Medication compliance on the web using role based access and using the web as the user interface;

Common prescription database on the web used as storage. All roles have the same medication database to avoid confusion and incorrect patient diagnosis/medication/dosage;

Common database for all roles for disease state management including ICD9 codes that can be used for reimbursement via CMS;

Ability to switch languages on the web application/ability to have the monitors language automatically be the language that patient sees the information on the web;

Monitor/Server/Web—mirrored databases. Security access—mirrored, limit access to the larger database where security concerns exist;

Send alerts via e-mail to others within the web application from the web application;

Change/program/configure the monitors and other devices used for health status collection via the web application interface;

Using color on the web to triage the status of the patients' information to determine priority for review.

Dual transmissions to the central station and the web to allow for redundancy in case of failure on either end. Backup and redundancy. Takes advantage that the web is an ancillary program and not the main program for monitoring patients.

Hover over alerts and use the hover over note for education by role via the web based on the vitals values, disease state, and medications.

Education by role on the web.

Vitals signs and patient hover to suggest appropriate topics based on parameters breaks to determine an algorithm that suggests role based education on the web.

Disease state and role based algorithm for determination of patient education on the web.

Web is the patient interface method to obtain patient education without using a pointer—but actually displaying the education on the web by role.

Compliance with education suggestions.

Method for tracking education tracking by patient and by role;

Method for entering medication changes.

Ability for doctor to push education to the patient via the web. Direct doctor to patient link for education.

Auto-refills and auto-delivery of patient medications via the web portal.

Patient portal that allows all care providers access to one central location for daily living activities:

Pharmacy
Doctor
Specialists
Physical therapy
Nursing Staff
Psychological/Psychiatric
Guardians Role/Access
Guardian ad lie tem
Family Members and Loved ones to view patient activities
ADL+
Medals on Wheels
Groceries purchase and delivery
Reimbursement sources
Insurance
Banking
Carbon Dioxide
Smoke detectors
Heating and Air Conditioning
Security System
DME
Utilities
Services in general to assist patient
Laboratory Results
Radiology Results
ER/Care Provider Roles
Local Hospital Access
Insurance Company Role Based Access to Appropriate materials Allows people that are responsible for certain needs of the patient access in one location to manage the needs of the patient based on the role type that they belong to.

Others have the ability to manage what is necessary for the daily living activities of a patient.

Wi-Fi or other wireless/remote access to ER.

Emergency/EMT/ER—additional role or roles could be incorporated.

From the foregoing, it will be observed that numerous variations and modifications may be effected without departing from the spirit and scope of the invention. It is to be understood that no limitation with respect to the specific apparatus illustrated herein is intended or should be inferred.

It is, of course, intended to cover by the appended claims all such modifications as fall within the scope of the claims.

The invention claim is:

1. A method comprising:
   establishing a database, the database comprising health related information associated with a plurality of different individuals;
   presenting a set-up display that enables a system administrator to define a plurality of levels of access to data in the database including a first read-only access level for each of the plurality of different individuals and their respective relatives and a second read and write access level for a respective physician of each of the plurality of individuals, said second access level providing access to information of the first access level for each of the plurality of individuals treated by the respective physician plus any determinations made and treatment options selected by the physician for the individual;
   providing a plurality of computer generated graphical displays that display the data of each of the plurality of individuals where each of the plurality of displays contains the data of only one individual, where each of the plurality of displays is associated with at least one of the plurality of levels of access and where at least one of the plurality of displays is a biometric graphic display associated with the individual;
   providing an access capability to a plurality of displaced users of the data in the database;
   receiving an access request from a user including an identifier of an individual of the plurality of individuals;
   evaluating the received access request and, determining if the user qualifies for access to the health information of the individual on at least one access level; and
   responsive to the determining, retrieving and forwarding to the user a graphics screen of the plurality of graphics screens including data from the database associated with the at least one access level and the individual.

2. A method as in claim 1 which includes enabling a user to specify selected portions of available data to be forwarded.

3. A method as in claim 2 where the access request includes a level specifying indicium.

4. A method as in claim 2 where the indicium comprises at least one of a predetermined binary sequence, or biometric information.

5. A method as in claim 4 where the biometric information comprises one of a voice print, at least one finger print, a facial scan, or an opthamological scan.

6. A method as in claim 4 which includes defining a class of users and associating respective access levels therewith.

7. A method as in claim 5 which includes associating a level specifying indicium with each member of the class.

8. A method as in claim 7 which includes enabling a user to enter a level specifying indicium associated therewith.

9. A method as in claim 8 which includes enabling the user to alter a previously established level specifying indicium.

10. A method as in claim 9 where a respective user only reviews received data.

11. A method as in claim 9 where a respective user carries out at least one of altering selected data, or supplementing selected data.

12. A method as in claim 1 which includes:
    establishing as the database health related information associated with each of a plurality of different individuals.

13. A method as in claim 10 wherein the database comprises health related information.

14. A method as in claim 13 where the user specifies an individual whose health related information is to be forwarded.

15. A method as in claim 14 where the user comprises one of the individual, or someone responsible for an aspect of the individual's health care.

16. An apparatus comprising:
    a processing unit and associated display device;
    a database of health related information associated with a plurality of different individuals;
    a plurality of user roles operable within the processing system including a first user read-only role of the user roles for each of the plurality of different individuals and their respective relatives and a second user read and write role of the roles for a respective physician of each of the plurality of individuals, said second read and write access level providing access to information of the first access level for each of the plurality of individuals treated by the respective physician plus any determinations made and treatment options selected by the physician for the individual;
    control software that provides a plurality of computer generated graphical displays that display the data of each of the plurality of individuals where each of the plurality of displays contains the data of only one individual, where each of the plurality of displays is associated with at least one of the plurality of levels of access and where at least one of the plurality of displays is a biometric graphic display associated with the individual; and
    control software, executable by the processing unit that evaluates a plurality of user requests for information where each user request includes an identifier of an individual of the plurality of individuals, that determines whether the user is authorized to access the health related information of the individual and that evaluates indicia indicative of the user's role based upon the user request and identifier of the individual and supplies role-limited information relative to the at least one individual within at least one of the plurality of screens, wherein the control software downloads the role-limited information to the user for access by the user and where an administrative setup screen is presented with a role-type specifying region.

17. An apparatus as in claim 16 where the user submits requests via an Internet service provider.

18. An apparatus as in claim 17 where role-limited reports relative to the one individual can be created.

19. An apparatus as in claim 17 where role-limited information is graphically presented in a color coded format.

20. An apparatus as in claim 16 which includes a second, primary database that couples updated information to the database on a predetermined basis.

* * * * *